(12) United States Patent
Miyashita et al.

(10) Patent No.: US 12,128,431 B2
(45) Date of Patent: Oct. 29, 2024

(54) PURIFYING APPARATUS AND PURIFYING METHOD

(71) Applicant: Panasonic Intellectual Property Management Co., Ltd., Osaka (JP)

(72) Inventors: Mariko Miyashita, Hyogo (JP); Tatsushi Ohyama, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 1240 days.

(21) Appl. No.: 16/842,890

(22) Filed: Apr. 8, 2020

(65) Prior Publication Data
US 2020/0230631 A1 Jul. 23, 2020

Related U.S. Application Data

(63) Continuation of application No. PCT/JP2018/038237, filed on Oct. 15, 2018.

(30) Foreign Application Priority Data

Oct. 31, 2017 (JP) .................................. 2017-211349
Oct. 2, 2018 (JP) .................................. 2018-187783

(51) Int. Cl.
*A61L 2/00* (2006.01)
*A61L 2/22* (2006.01)
(Continued)

(52) U.S. Cl.
CPC .............. *B05B 12/124* (2013.01); *A61L 2/22* (2013.01); *G01N 21/64* (2013.01); *G01N 21/94* (2013.01);
(Continued)

(58) Field of Classification Search
CPC . A61L 2/0088; A61L 2/18; A61L 2/24; A61L 9/14; A61L 2202/15; G01N 21/6447; B05C 1/00
(Continued)

(56) References Cited

U.S. PATENT DOCUMENTS

2003/0160182 A1* 8/2003 Petrich ............... G01N 21/6447
250/461.1
2011/0026029 A1 2/2011 Iwasaki et al.
2015/0119722 A1 4/2015 Kaneko

FOREIGN PATENT DOCUMENTS

CN 104784853 A 7/2015
JP 2004-008230 1/2004
(Continued)

OTHER PUBLICATIONS

English Translation of Chinese Search Report dated Oct. 25, 2022 for the related Chinese Patent Application No. 201880057520.2.
(Continued)

*Primary Examiner* — Monzer R Chorbaji
(74) *Attorney, Agent, or Firm* — Rimon P.C.

(57) ABSTRACT

A purifying apparatus includes: an optical sensor that outputs an electrical signal, the optical sensor including a light source that emits first light and a photodetector that receives second light from a region irradiated with the first light; a determination circuit that determines the presence or absence of a physical object in the region and generates an image representing a determination result, the determination circuit including a signal processing circuit that processes the electrical signal; a spray that sprays a cleansing agent through a spray nozzle, the spray including the spray nozzle; a range finder that measures a distance from the spray nozzle to the physical object; and a controller that controls, according to the distance, spraying of the cleansing agent by the spray.

13 Claims, 25 Drawing Sheets

(51) Int. Cl.
*A61N 5/00* (2006.01)
*B05B 12/12* (2006.01)
*G01N 21/00* (2006.01)
*G01N 21/64* (2006.01)
*G01N 21/94* (2006.01)

(52) U.S. Cl.
CPC .... *A61L 2202/15* (2013.01); *G01N 2021/945* (2013.01)

(58) Field of Classification Search
USPC ......... 422/22, 24; 250/455.11, 454.11, 292.1
See application file for complete search history.

(56) References Cited

FOREIGN PATENT DOCUMENTS

| JP | 2004-294337 | 10/2004 |
|----|-------------|---------|
| JP | 2007-113996 | 5/2007 |
| JP | 2008-022776 | 2/2008 |
| JP | 2010-185719 | 8/2010 |
| JP | 2010-266380 | 11/2010 |
| JP | 2013-000383 | 1/2013 |
| JP | 2015-108508 | 6/2015 |
| JP | 2015-180895 | 10/2015 |
| JP | 2017-003541 | 1/2017 |
| WO | 2009/123068 | 10/2009 |
| WO | 2013/187148 | 12/2013 |

OTHER PUBLICATIONS

International Search Report of PCT application No. PCT/JP2018/038237 dated Jan. 15, 2019.

Thanko Kabushikikaisya, "News Release, Endoscope + high pressure washer Launched, "Industrial endoscope side view model with cleaning function"", Feb. 2, 2017, pp. 1-3, <URL:https://kyodonewsprwire.jp/prwfile/release/M100177/201702028438/_prw_PR1fl_njfHTlih.pdf>.

* cited by examiner

PURIFYING APPARATUS AND PURIFYING METHOD

BACKGROUND

1. Technical Field

The present disclosure relates to a purifying apparatus and a purifying method.

2. Description of the Related Art

In recent years, transmission of disease by infection through vomit or the like has become a social issue. For example, a norovirus-infected person's vomit is said to contain one million viruses or more per 1 g. For this reason, a large number of cases have been reported where the presence of a slight residue due to an insufficient vomit-cleaning process resulted in a large number of secondary infection patients.

For inhibition of secondary infection, it is expected that a cleaning process is sufficiently performed. However, the presence or absence of residue after cleaning is usually visually checked by a cleaning person. For this reason, a cleaning process is hardly always sufficiently performed, as the degree of completion of a cleaning process depends on the ability of a cleaning person. Further, a visual check is burdensome for a cleaning person.

Under such circumstances, there is demand for a method for more easily detecting residue. In this regard, for inhibition of infection by viruses contained in residue, it is desirable that residue be detectable in a noncontact manner.

SUMMARY

In one general aspect, the techniques disclosed here feature a purifying apparatus including: an optical sensor that outputs an electrical signal, the optical sensor including a light source that emits first light and a photodetector that receives second light from a region irradiated with the first light; a determination circuit that determines the presence or absence of a physical object in the region and generates an image representing a determination result, the determination circuit including a signal processing circuit that processes the electrical signal; a container in which a cleansing agent is stored; a spray that sprays the cleansing agent through a spray nozzle, the spray including the spray nozzle; and a portable housing in which the optical sensor, the determination circuit, the spray, and the container are housed.

In one general aspect, the techniques disclosed here feature a purifying apparatus including: an optical sensor that outputs an electrical signal, the optical sensor including a light source that emits first light and a photodetector that receives second light from a region irradiated with the first light; a determination circuit that determines the presence or absence of a physical object in the region and generates an image representing a determination result, the determination circuit including a signal processing circuit that processes the electrical signal; a spray that sprays a cleansing agent through a spray nozzle, the spray including the spray nozzle; a range finder that measures a distance from the spray nozzle to the physical object; and a controller that controls, according to the distance, spraying of the cleansing agent by the spray.

In one general aspect, the techniques disclosed here feature a purifying method including: determining, based on an electrical signal outputted from an optical sensor including a light source that emits first light and a photodetector that receives second light from a region irradiated with the first light, the presence or absence of a physical object in the region; spraying a cleansing agent through a spray nozzle; measuring a distance from the spray nozzle to the physical object; and controlling, according to the distance, spraying of the cleansing agent by the spray.

One aspect of the present disclosure can be achieved as a program for causing a computer to execute a method for controlling the purifying apparatus. Alternatively, it can also be achieved as a computer-readable recording medium having the program stored thereon.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
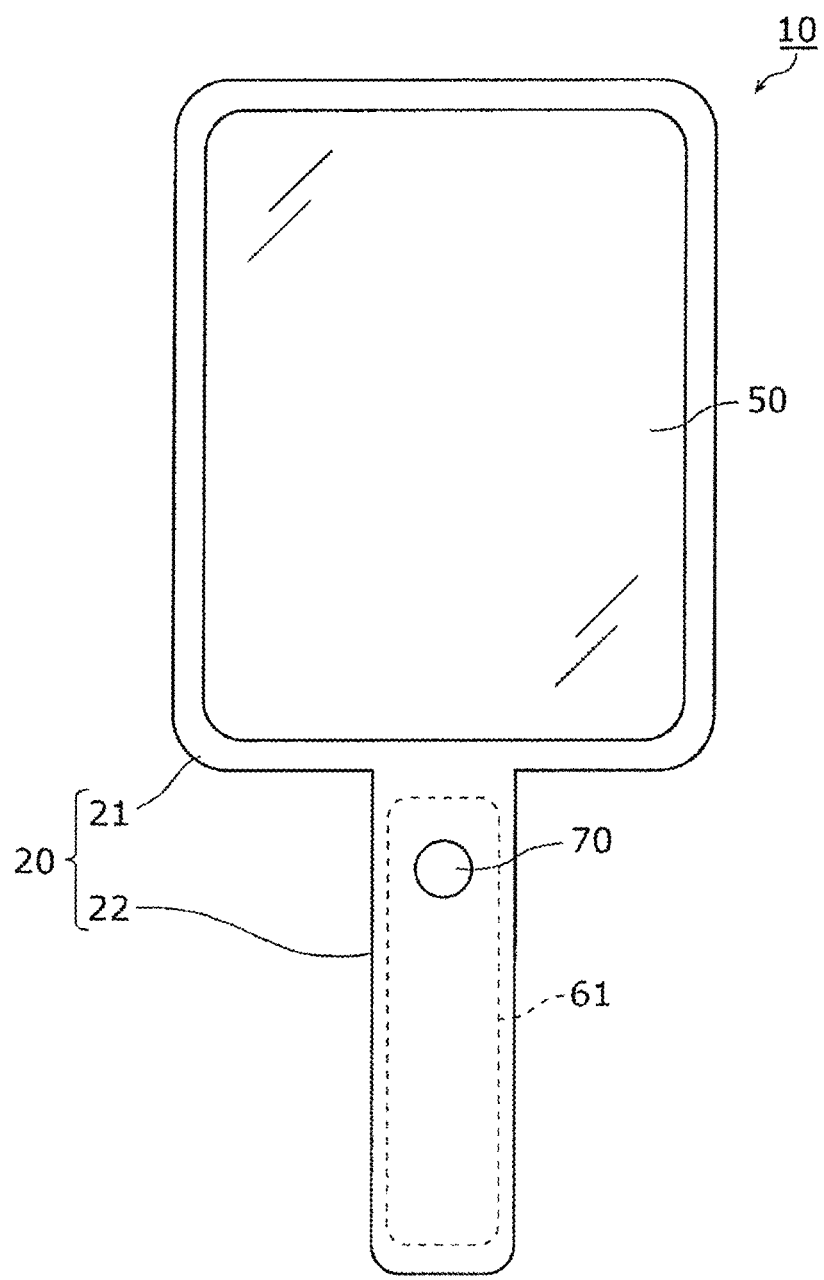
FIG. 1 is a front view of a purifying apparatus according to Embodiment 1.

For example, Japanese Unexamined Patent Application Publication No. 2010-185719, Japanese Patent No. 3706914, Japanese Unexamined Patent Application Publication No. 2010-266380, International Publication No. 2009/123068, and Japanese Patent No. 5985709 disclose methods for optically detecting a physical object. Specifically, by irradiating a physical object with excitation light and detecting fluorescence that is emitted from the physical object excited by the excitation light, the class or the like of the physical object can be determined.

However, the methods disclosed in Japanese Unexamined Patent Application Publication No. 2010-185719, Japanese Patent No. 3706914, Japanese Unexamined Patent Application Publication No. 2010-266380, International Publication No. 2009/123068, and Japanese Patent No. 5985709 are hardly applicable in general environments such as the interiors of rooms, as a physical object to be detected needs to be placed within a detection apparatus. Further, there is no way of removing a detected physical object on the spot.

One non-limiting and exemplary embodiment provides a purifying apparatus and a purifying method that make it possible to perform a simple operation starting with detection of a physical object and ending with removal of the physical object thus detected.

BRIEF OVERVIEW OF THE PRESENT DISCLOSURE

In one general aspect, the techniques disclosed here feature a purifying apparatus including: an optical sensor having a light source and a photodetector that receives second light from a region irradiated with first light emitted by the light source; a determination circuit that determines the presence or absence of a physical object in the region and generates an image representing a determination result, the determination circuit including a signal processing circuit that processes an electrical signal outputted from the optical sensor; a display that display the image generated by the determination circuit; and a spray that has a container in which a cleansing agent for removing the physical object is contained and a spray nozzle through which the cleansing agent is sprayed and that sprays the cleansing agent through the spray nozzle.

This makes it possible to perform a simple operation starting with detection of a physical object and ending with removal of the physical object thus detected, as the purifying apparatus includes the determination circuit and the spray and sprays the cleansing agent on the basis of a result of a determination of the presence or absence of a physical object.

In one general aspect, the techniques disclosed here feature a purifying apparatus including: an optical sensor that outputs an electrical signal, the optical sensor including a light source that emits first light and a photodetector that receives second light from a region irradiated with the first light; a determination circuit that determines the presence or absence of a physical object in the region and generates an image representing a determination result, the determination circuit including a signal processing circuit that processes the electrical signal; a container in which a cleansing agent is stored; a spray that sprays the cleansing agent through a spray nozzle, the spray including the spray nozzle; and a portable housing in which the optical sensor, the determination circuit, the spray, and the container are housed.

This makes it possible to perform a simple operation starting with detection of a physical object and ending with removal of the physical object thus detected, as the optical sensor, the determination circuit, the spray, and the container are housed in the portable housing. Further, the excellence in portability makes it possible to easily carry around the purifying apparatus to a place where a physical object to be removed may be present and makes it possible to determine the presence or absence of a physical object in various places and remove the physical object.

Further, for example, the first light may be excitation light that excites the physical object, and the second light may be fluorescence that the physical object emits upon irradiation with the excitation light.

This makes it possible to determine the presence or absence of a physical object with high accuracy on the basis of the wavelength, intensity, and the like of fluorescence, as fluorescence emitted from a physical object can be received by the photodetector. Accordingly, with an increase in accuracy of determination, failed detection of a physical object can be reduced, and the physical object can be sufficiently removed.

Further, for example, the determination circuit may determine the presence or absence of the physical object based on a combination of a wavelength of the fluorescence and a wavelength of the excitation light.

This makes it possible to further increase the accuracy of detection of a physical object in a case where the optical sensor is constituted by a combination corresponding to a physical object to be detected. For example, in a case where the physical object to be detected is a physical object containing an amino acid tryptophan, tryptophan is known to emit fluorescence at a wavelength of around 360 nm upon irradiation with excitation light at a wavelength of 280 nm. Accordingly, the amino acid tryptophan can be detected with high accuracy by causing the light source to emit excitation light at a wavelength of 280 nm and extracting a wavelength component of 360 nm from light received by the photodetector.

Further, for example, the determination circuit may determine the presence or absence of the physical object based on a result of a comparison between an intensity of the second light received by the photodetector and a threshold.

This makes it possible to reduce throughput required for a determination process, as the presence or absence of a physical object can be determined by a comparison process.

Further, for example, the determination circuit may determine the presence or absence of the physical object based on a component of the second light whose wavelength is longer than a wavelength of the first light.

This makes it possible to reduce the influence of a reflection of the first light or the like and increase the accuracy of detection of a physical object, as the presence or absence of a physical object is determined on the basis of a wavelength component that is different from the first light emitted.

Further, for example, the purifying apparatus according to the aspect of the present disclosure may further include a housing that forms an outer shell of the purifying apparatus, and the housing may have a handle.

This makes it possible to achieve a highly portable purifying apparatus, as the housing that forms the outer shell of the purifying apparatus has the handle. This makes it possible easily carry around the purifying apparatus to a place where a physical object may be present and makes it possible to determine the presence or absence of a physical object in various places and remove the physical object. This makes it possible, for example, to detect a physical object over a wide range and reduce failed detection of the physical object.

Further, for example, the purifying apparatus according to the aspect of the present disclosure may further include an operation button, provided to the handle, that at least either causes the light source to emit the first light or causes the spray to spray the cleansing agent.

This makes it possible to detect or remove a physical object at any given timing based on an operation from the user. Further, the provision of the operation button to the handle allows the user to operate the operation button with a finger or the like while holding the handle. This makes it possible to achieve a highly operable purifying apparatus.

Further, for example, the container may be provided inside the handle.

This makes it possible to effectively utilize space in the handle, so that a reduction in size of the purifying apparatus is achieved.

Further, for example, the purifying apparatus according to the aspect of the present disclosure may further include a range finder that measures a distance to the physical object, and the spray may control, according to the distance measured by the range finder, conditions under which the cleansing agent is sprayed.

This makes it possible to increase the probability of contact between the cleansing agent and a physical object, thus making it possible to efficiently remove the physical object.

Further, for example, the conditions under which the cleansing agent is sprayed may be a pressure at which the cleansing agent is sprayed.

This makes it possible to easily adjust a flying distance of the cleansing agent by adjusting the spraying pressure and makes it possible to easily remove a physical object even from a distance. Since there is no need to bring the physical object and the purifying apparatus into contact with each other, the purifying apparatus per se can be kept clean.

At this point in time, for example, the influence of gravity on the cleansing agent sprayed from the spray nozzle varies, depending on whether the spray nozzle faces upward or faces downward. To address this problem, the purifying apparatus according to the aspect of the present disclosure may further include an angular sensor that detects a tilt of the purifying apparatus, and the spray may control a mode of spraying of the cleansing agent according to a distance measured by the range finder and a tilt detected by the angular sensor.

This makes it possible to further increase the probability of contact between the cleansing agent and a physical object, thus making it possible to further efficiently remove the physical object.

Further, for example, the physical object may be vomit, excrement, or body fluids.

This makes it possible to remove viruses contained in vomit or the like and makes it possible to reduce transmission such as secondary infection.

Further, for example, the cleansing agent may be a sodium hypochlorite formulation or an alcohol formulation.

This makes it possible to remove viruses or the like contained in the physical object, if any, and makes it possible to reduce transmission such as secondary infection.

In one general aspect, the techniques disclosed here feature a purifying apparatus including: an optical sensor that outputs an electrical signal, the optical sensor including a light source that emits first light and a photodetector that receives second light from a region irradiated with the first light; a determination circuit that determines the presence or absence of a physical object in the region and generates an image representing a determination result, the determination circuit including a signal processing circuit that processes the electrical signal; a spray that sprays a cleansing agent through a spray nozzle, the spray including the spray nozzle; a range finder that measures a distance from the spray nozzle to the physical object; and a controller that controls, according to the distance, spraying of the cleansing agent by the spray.

This makes it possible to perform a simple operation starting with detection of a physical object and ending with removal of the physical object thus detected, as the optical sensor, the determination circuit, and the spray are provided. Further, the cleansing agent can be sprayed toward the physical object with high accuracy, as how the cleansing agent is sprayed is controlled according to the distance measured by the range finder. This makes it possible to increase the probability of contact between the cleansing agent and the physical object and makes it possible to efficiently remove the physical object.

Further, for example, the purifying apparatus may further include an angular sensor that detects a tilt of the spray nozzle with respect to an imaginary plane that is perpendicular to a direction of gravitational force, and the controller may control, according to either a combination of the distance and a pressure at which the spray sprays the cleansing agent or a combination of the distance and the tilt of the spray nozzle, conditions under which the cleansing agent is sprayed.

This makes it possible to spray the cleansing agent toward the physical object with high accuracy, as the mode of spraying is controlled on the basis of the pressure during spraying or the tilt of the spray nozzle as well as the distance to the physical object. This makes it possible to increase the probability of contact between the cleansing agent and the physical object and makes it possible to efficiently remove the physical object.

Further, for example, the controller may accept a first choice of a tilt during spraying by a user, the first choice of the tilt during spraying being a tilt of the spray nozzle with respect to the imaginary plane during spraying of the cleansing agent, in a case where the tilt during spraying is a tilt pointing to a lower position than the imaginary plane, the controller may calculate a first pressure that allows the cleansing agent to reach the physical object and cause the cleansing agent to be sprayed from the spray nozzle at the first pressure, and in a case where the tilt during spraying is a tilt pointing toward a higher position than the imaginary plane, the controller may calculate a second pressure that is higher than the first pressure and cause the cleansing agent to be sprayed from the spray nozzle at the second pressure.

This makes it possible to highly accurately calculate a pressure at which the cleansing agent is sprayed toward a higher position or a lower position than the imaginary plane. This makes it possible to spray the cleansing agent toward the physical object with high accuracy and makes it possible to efficiently remove the physical object.

The purifying apparatus may further include a display that displays a first trajectory of reach from the spray nozzle to the physical object when the first pressure has been calculated and that displays a second trajectory of reach from the spray nozzle to the physical object when the second pressure has been calculated.

This makes it possible to give the user a schematic presentation of how the cleansing agent is sprayed, as a trajectory of reach of the cleansing agent is displayed.

Further, for example, the display may display the first trajectory of reach and the first pressure when the first pressure has been calculated and display the second trajectory of reach and the second pressure when the second pressure has been calculated.

This allows the user to utilize the displayed pressure as information for making a decision as to selection of a trajectory of reach. That is, the user can be assisted in making a proper selection, and the physical object can be efficiently removed.

The controller may further accept a second choice of the tilt during spraying by the user, in a case where the tilt during spraying of the first choice is a tilt pointing toward a lower position than the imaginary plane and the tilt during spraying of the second choice is a tilt pointing toward a higher position than the imaginary plane or in a case where the tilt during spraying of the first choice is a tilt pointing toward a higher position than the imaginary plane and the tilt during spraying of the second choice is a tilt pointing toward a lower position than the imaginary plane, the display may simultaneously display the first trajectory of reach and the second trajectory of reach, and the controller may accept selection of either the first trajectory of reach or the second trajectory of reach and cause the cleansing agent to be sprayed from the spray nozzle at a pressure that corresponds to the trajectory of reach thus selected.

This allows the user to select a trajectory of reach, thus making it possible to enhance user-friendliness.

Further, for example, the display may display recommendation information that recommends selection of the first trajectory of reach.

This makes it possible to assist the user in making a proper selection and makes it possible to efficiently remove the physical object.

In one general aspect, the techniques disclosed here feature a purifying method including: determining, based on an electrical signal outputted from an optical sensor including a light source that emits first light and a photodetector that receives second light from a region irradiated with the first light, the presence or absence of a physical object in the region; spraying a cleansing agent through a spray nozzle; measuring a distance from the spray nozzle to the physical object; and controlling, according to the distance, spraying of the cleansing agent by the spray.

This makes it possible to perform a simple operation starting with detection of a physical object and ending with removal of the physical object thus detected, as the presence or absence of the physical object is determined and the physical object is removed. Further, the cleansing agent can be sprayed toward the physical object with high accuracy, as how the cleansing agent is sprayed is controlled according to the distance thus measured. This makes it possible to increase the probability of contact between the cleansing agent and the physical object and makes it possible to efficiently remove the physical object.

Further, for example, the purifying method may further include detecting a tilt of the spray nozzle with respect to an imaginary plane that is perpendicular to a direction of gravitational force, and the controlling may include controlling, according to either a combination of the distance and a pressure at which the spray sprays the cleansing agent or a combination of the distance and the tilt of the spray nozzle, conditions under which the cleansing agent is sprayed.

This makes it possible to spray the cleansing agent toward the physical object with high accuracy, as the mode of spraying is controlled on the basis of the pressure during spraying or the tilt of the spray nozzle as well as the distance to the physical object. This makes it possible to increase the probability of contact between the cleansing agent and the physical object and makes it possible to efficiently remove the physical object.

Further, for example, the purifying method may further include accepting a first choice of a tilt during spraying by a user, the first choice of the tilt during spraying being a tilt of the spray nozzle with respect to the imaginary plane during spraying of the cleansing agent, and the controlling may include, when a tilt pointing to a lower position than the imaginary plane has been chosen as the tilt during spraying, calculating a first pressure that allows the cleansing agent to reach the physical object and causing the cleansing agent to be sprayed from the spray nozzle at the first pressure, and when a tilt pointing toward a higher position than the imaginary plane has been chosen as the tilt during spraying, calculating a second pressure that is higher than the first pressure and causing the cleansing agent to be sprayed from the spray nozzle at the second pressure.

This makes it possible to highly accurately calculate a pressure at which the cleansing agent is sprayed toward a higher position or a lower position than the imaginary plane. This makes it possible to spray the cleansing agent toward the physical object with high accuracy and makes it possible to efficiently remove the physical object.

Further, for example, the purifying method may further include displaying a first trajectory of reach from the spray nozzle to the physical object on a display when the first pressure has been calculated and displaying a second trajectory of reach from the spray nozzle to the physical object on the display when the second pressure has been calculated.

This makes it possible to give the user a schematic presentation of how the cleansing agent is sprayed, as a trajectory of reach of the cleansing agent is displayed.

Further, for example, the displaying may include displaying the first trajectory of reach and the first pressure on the display when the first pressure has been calculated and displaying the second trajectory of reach and the second pressure on the display when the second pressure has been calculated.

This allows the user to utilize the displayed pressure as information for making a decision as to selection of a trajectory of reach. That is, the user can be assisted in making a proper selection, and the physical object can be efficiently removed.

The purifying method may further include accepting a second choice of the tilt during spraying by the user, in a case where the tilt during spraying of the first choice is a tilt pointing toward a lower position than the imaginary plane and the tilt during spraying of the second choice is a tilt pointing toward a higher position than the imaginary plane or in a case where the tilt during spraying of the first choice is a tilt pointing toward a higher position than the imaginary plane and the tilt during spraying of the second choice is a tilt pointing toward a lower position than the imaginary plane, the displaying may include simultaneously displaying the first trajectory of reach and the second trajectory of reach on the display, and the controlling may include accepting selection of either the first trajectory of reach or the second trajectory of reach and causing the cleansing agent to be sprayed from the spray nozzle at a pressure that corresponds to the trajectory of reach thus selected.

This allows the user to select a trajectory of reach, thus making it possible to enhance user-friendliness.

Further, for example, the displaying may include displaying, on the display, recommendation information that recommends selection of the first trajectory of reach.

This makes it possible to assist the user in making a proper selection and makes it possible to efficiently remove the physical object.

Further, for example, the first light may be excitation light that excites the physical object, and the second light may be fluorescence that the physical object emits upon irradiation with the excitation light.

This makes it possible to determine the presence or absence of a physical object with high accuracy on the basis of the wavelength, intensity, and the like of fluorescence, as fluorescence emitted from a physical object can be received by the photodetector. Accordingly, with an increase in accuracy of determination, failed detection of a physical object can be reduced, and the physical object can be sufficiently removed.

Further, for example, the determining may include determining the presence or absence of the physical object based on a combination of a wavelength of the fluorescence and a wavelength of the excitation light.

This makes it possible to further increase the accuracy of detection of a physical object in a case where the optical sensor is constituted by a combination corresponding to a physical object to be detected.

Further, for example, the determining may include determining the presence or absence of the physical object based on a result of a comparison between an intensity of the second light received by the photodetector and a threshold.

This makes it possible to reduce throughput required for a determination process, as the presence or absence of a physical object can be determined by a comparison process.

Further, for example, the determining may include determining the presence or absence of the physical object based on a component of the second light whose wavelength is longer than a wavelength of the first light.

This makes it possible to reduce the influence of a reflection of the first light or the like and increase the accuracy of detection of a physical object, as the presence or absence of a physical object is determined on the basis of a wavelength component that is different from the first light emitted.

In the present disclosure, all or a part of any of circuit, unit, device, part or portion, or any of functional blocks in the block diagrams may be implemented as one or more of electronic circuits including, but not limited to, a semiconductor device, a semiconductor integrated circuit (IC) or an LSI. The LSI or IC can be integrated into one chip, or also can be a combination of plural chips. For example, functional blocks other than a memory may be integrated into one chip. The name used here is LSI or IC, but it may also be called system LSI, VLSI (very large scale integration), or ULSI (ultra large scale integration) depending on the degree of integration. A Field Programmable Gate Array (FPGA) that can be programmed after manufacturing an LSI or a reconfigurable logic device that allows reconfiguration of the connection or setup of circuit cells inside the LSI can be used for the same purpose.

Further, it is also possible that all or a part of the functions or operations of the circuit, unit, device, part or portion are implemented by executing software. In such a case, the software is recorded on one or more non-transitory recording media such as a ROM, an optical disk or a hard disk drive, and when the software is executed by a processor, the software causes the processor together with peripheral devices to execute the functions specified in the software. A system or apparatus may include such one or more non-transitory recording media on which the software is recorded and a processor together with necessary hardware devices such as an interface.

The following describes embodiments in concrete terms with reference to the drawings.

It should be noted that the embodiments to be described below illustrate general or specific examples. The numerical values, shapes, materials, constituent elements, locations of placement and forms of connection of constituent elements, steps, and orders of steps that are shown in the following embodiments are mere examples and are not intended to limit the present disclosure. Further, those of the constituent elements according to the following embodiments which are not recited in an independent claim are described as optional constituent elements.

Further, the drawings are schematic views and are not necessarily strict illustrations. Accordingly, for example, the drawings are not necessarily to scale. Further, the drawings assign identical signs to substantially identical components and omit or simplify repeated descriptions.

Embodiment 1

1. Configuration

Figure 2:
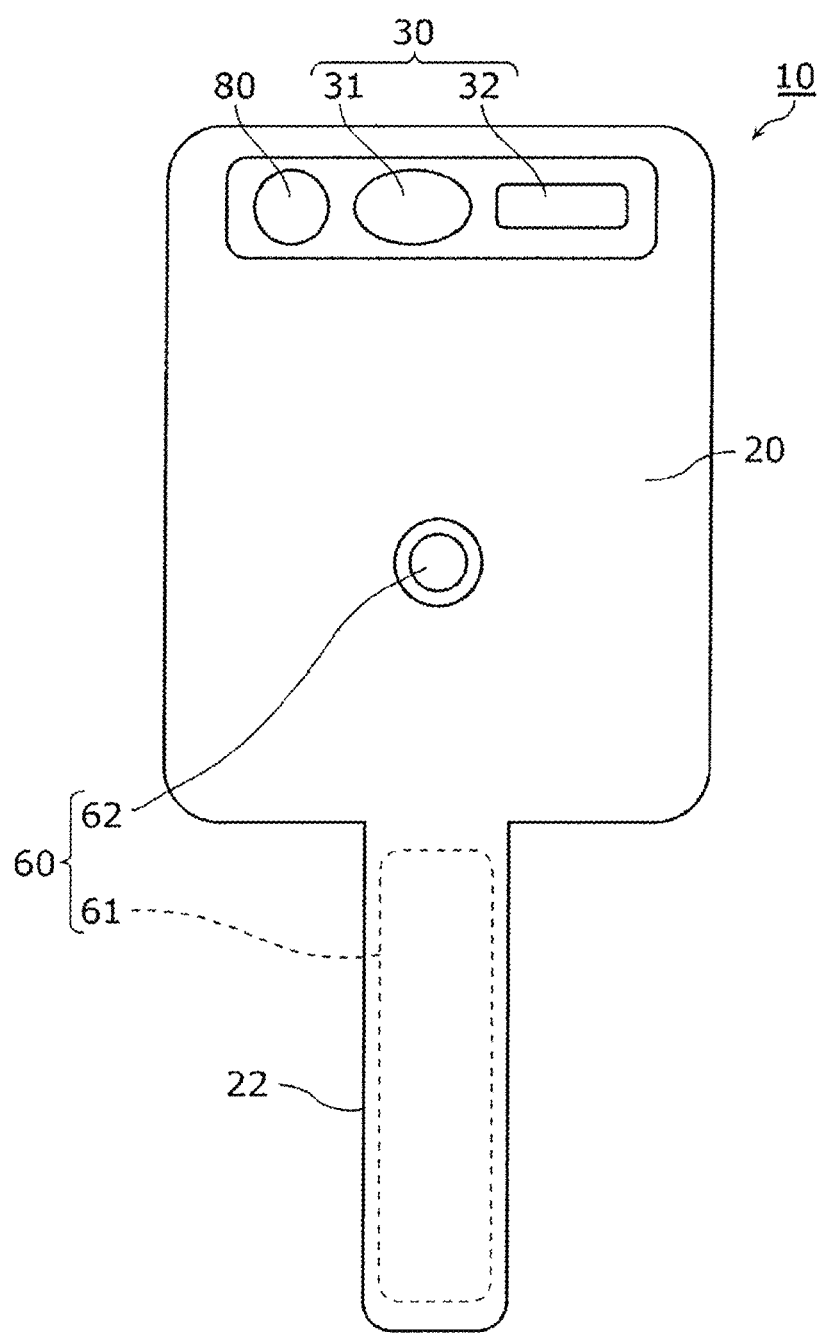
FIG. 2 is a back view of the purifying apparatus according to Embodiment 1.
Figure 3:
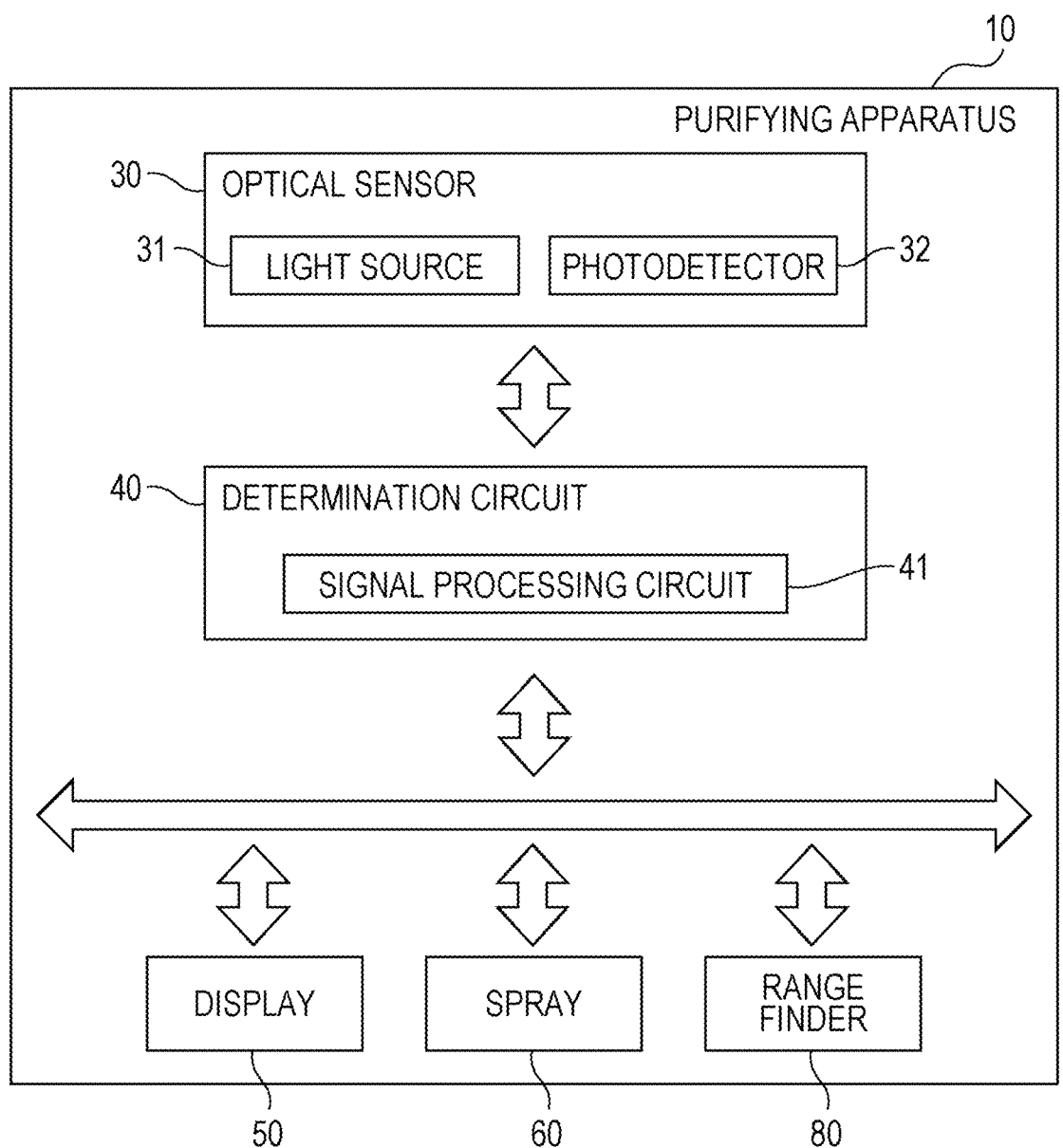
FIG. 3 is a block diagram showing a configuration of the purifying apparatus according to Embodiment 1.

First, a brief overview of a purifying apparatus according to Embodiment 1 is provided with reference to FIGS. 1 to 3.

FIGS. 1 and 2 are a front view and a back view, respectively, of a purifying apparatus 10 according to Embodiment 1. FIG. 3 is a block diagram showing a configuration of the purifying apparatus 10 according to Embodiment 1.

In Embodiment 1, the purifying apparatus 10 has its front surface serving as a side on which a display 50 has its display surface provided. The purifying apparatus 10 has its back surface on a side opposite to the front surface. In Embodiment 1, as shown in FIG. 2, the purifying apparatus 10 has an optical sensor 30, a spray nozzle 62 of a spray 60, or other components provided on a back side thereof.

The purifying apparatus 10 is an apparatus that performs an integrated operation starting with detection of a physical object and ending with removal of the physical object thus detected. In Embodiment 1, the purifying apparatus 10 performs detection and removal of a physical object in a noncontact manner. Specifically, the purifying apparatus 10 optically detects a physical object in a region distant from the purifying apparatus 10 and sprays a cleansing agent toward the physical object thus detected, thereby performing removal of the physical object.

Examples of physical objects include substances, such as vomit, excrement, or body fluids, discharged by humans. Alternatively, physical objects may be food materials or food products. Physical objects contain microorganisms, such as viruses or bacteria, that can cause human disease. In Embodiment 1, a physical object contains an organic substance and, upon irradiation with excitation light of a predetermined wavelength, emits fluorescence. Examples of organic substances include, but are not limited to, amino acids that are contained in high proportions in food products or organisms. An amino acid emits fluorescence at around 320 nm, for example, upon irradiation with excitation light at around 280 nm.

The cleansing agent is an agent for removing a physical object. Removal of a physical object means for example rendering the physical object harmless by degrading microorganisms, such as viruses or bacteria, contained in the physical object. The cleansing agent is for example a sodium hypochlorite formulation or an alcohol formulation. The cleansing agent is for example a liquid but may be a gas or a solid.

As shown in FIGS. 1 to 3, the purifying apparatus 10 includes a housing 20, the optical sensor 30, a determination circuit 40, the display 50, the spray 60, an operation button 70, and a range finder 80. In the following, each of the constituent elements that constitute the purifying apparatus 10 is described in detail.

The housing 20 forms an outer shell of the purifying apparatus 10. As shown in FIGS. 1 and 2, the housing 20 includes a frame 21 and a handle 22.

The frame 21 is a part that mainly retains the display 50, and is constructed in the shape of a flat tray. As shown in FIG. 1, the frame 21 has a front side on which the display surface of the display 50 is exposed. As shown in FIG. 2, the frame 21 has a back side on which the optical sensor 30, the spray nozzle 62 of the spray 60, and the range finder 80 are exposed. It should be noted that the illustrated example is not intended to restrict the placement of the optical sensor 30, the spray nozzle 62, and the range finder 80.

The handle 22 is a part for a person to hold with one hand or both hands. As shown in FIGS. 1 and 2, the handle 22 is a rod-shaped part provided to extend in one direction from a portion of the frame 21. The handle 22 has, but is not limited to, a columnar shape or a prismatic shape.

In Embodiment 1, as shown in FIG. 1, the handle 22 is provided with the operation button 70 for the spray 60. The operation button 70 is provided, for example, on a front surface of the handle 22. The operation button 70 is provided in an area where, in a case where the handle 22 is held with one hand, the operation button 70 can be operated with the thumb.

As shown in FIG. 2, the optical sensor 30 has a light source 31 and a photodetector 32. The optical sensor 30 outputs, to a signal processing circuit 41 of the determination circuit 40, an electrical signal generated by the photodetector 32.

The light source 31 emits excitation light that excites a physical object. The excitation light is an example of first light that the light source 31 emits. The excitation light is light that has a peak at a wavelength selected in advance according to the type of physical object to be detected. A half-value width of the peak of the excitation light falls within a range of, for example, 10 nm or greater to 50 nm or less.

In Embodiment 1, the light source 31 emits, as the first light, a plurality of rays of excitation light of different wavelengths from each other. Specifically, the light source 31 emits a plurality of rays of excitation light in a time exclusive manner. For example, the light source 31 sequentially emits a plurality of rays of excitation light having wavelengths of 280 nm, 350 nm, and 450 nm, respectively. It should be noted that these excitation wavelengths are merely examples and, for example, may be selected as appropriate from among arbitrary wavelengths according to the type of physical object or the like.

For example, the light source 31 may irradiate a physical object with excitation light with time-continuous variations in wavelength. For example, the light source 31 may irradiate a physical object with a plurality of rays of excitation light of different wavelengths from each other in sequence with variations in wavelength in 10-nm increments in a range of 220 nm or longer to 550 nm or shorter.

Alternatively, the light source 31 may have its light exit side provided with a plurality of filters of different transmission bands. Sequential changes of filters of the plurality of filters through which light emitted from the light source 31 passes makes it possible to irradiate a physical object with a plurality of rays of excitation light of different wavelengths from each other in sequence.

Examples of the light source 31 include, but are not limited to, a discharge lamp such as a halogen lamp or a solid-state light-emitting element such as an LED (light-emitting diode).

The photodetector 32 receives second light from an irradiated region irradiated with the first light emitted by the light source 31. For example, the irradiated region with the first light emitted by the light source 31 and a region of photodetection (i.e. a range of shooting) by the photodetector 32 overlap or coincide with each other.

The photodetector 32 is specifically an image sensor having a plurality of pixels arrayed in a two-dimensional state. Each of the plurality of pixels includes a photoelectric conversion element, such as a photodiode, that photoelectrically converts received light. Processing electrical signals outputted from each separate pixel of the photodetector 32 generates a shot image.

In Embodiment 1, the photodetector 32 receives incident light as the second light in a wavelength-selective manner. Specifically, with variations in wavelength (i.e. observed wavelength) of the second light to be received, the photodetector 32 generates and outputs electrical signals that represent reception intensities for each separate observed wavelength.

For example, the photodetector 32 has a plurality of filters, placed on a light entrance side of the photoelectric conversion element, whose transmission bands are different from each other. The transmission bands of the filters are equivalent to observed wavelengths by the photodetector 32. The photodetector 32 receives light of different wavelengths by switching the plurality of filters in a time exclusive manner. For example, the photodetector 32 sequentially receives a plurality of rays of light having wavelengths of 310 nm, 425 nm, and 520 nm, respectively. It should be noted that these observed wavelengths are merely examples and, for example, may be selected as appropriate from among arbitrary wavelengths according to the type of physical object or the like.

The determination circuit 40 determines the presence or absence of a physical object in the irradiated region and generates an image representing a determination result. The determination circuit 40 is achieved, for example, by a nonvolatile memory in which a program is stored, a volatile memory serving as a transitory recording region in which to execute the program, an I/O port, a processor that executes the program, or other components.

As shown in FIG. 3, the determination circuit 40 has the signal processing circuit 41, which processes an electrical signal outputted from the optical sensor 30. The signal processing circuit 41 is achieved, for example, by an integrated circuit including one or more electronic circuits.

The determination circuit 40 determines the presence or absence of a physical object on the basis of a combination of a wavelength of fluorescence and a wavelength of excitation light. Specifically, the determination circuit 40 determines the presence or absence of a physical object for each pixel of the photodetector 32. This enables the determination circuit 40 to determine where in the range of shooting a physical object is present and, in a case where a physical object is present, determine the size, shape, or other features of the physical object.

In Embodiment 1, the determination circuit 40 performs a determination process for each pixel through the use of fluorescence fingerprints. A determination process involving the use of fluorescence fingerprints will be described in detail later.

The display 50 displays an image generated by the determination circuit 40. Further, the display 50 displays a shot image generated by the photodetector 32. The display 50 is for example a flat-panel display such as a liquid crystal display device or an organic EL (electroluminescence) display device.

The spray 60 has a container 61 in which a cleansing agent for removing a physical object is contained and the spray nozzle 62, through which the cleansing agent is sprayed, and sprays the cleansing agent through the spray nozzle 62 on the basis of a determination result. For example, the spray 60 atomizes the cleansing agent in the form of a mist through the spray nozzle 62. The spray 60 includes a control circuit (not illustrated) or other components. The control circuit is achieved, for example, by an integrated circuit including one or more electronic circuits and controls the timing of spraying of the cleansing agent, the mode of spraying of the cleansing agent, and the like.

The container 61 is provided inside the handle 22. The container 61 is detachable from the handle 22. For example, the container 61 is a cartridge container in which the cleansing agent is contained in advance. Specifically, the handle 22 is constructed in the shape of a cylinder into which the container 61 is inserted through an end thereof. The insertion of the container 61 into a predetermined position causes the container 61 and the spray nozzle 62 to be connected for attachment in a state where the cleansing agent in the container 61 can be sprayed through the spray nozzle 62. For example, in a case where a user has operated the operation button 70 with the container 61 inserted in the handle 22, the cleansing agent is sprayed from the spray nozzle 62.

In Embodiment 1, the spray 60 controls the mode of spraying of the cleansing agent according to a distance measured by the range finder 80. The mode of spraying of the cleansing agent is specifically a pressure at which the cleansing agent is sprayed. The spray 60 changes, on the basis of the distance measured by the range finder 80, the pressure at which the cleansing agent is sprayed.

For example, the longer a distance to a physical object is, the higher pressure the spray 60 sprays the cleansing agent at. This makes it possible to bring the cleansing agent into contact with a remotely-located physical object and remove the physical object. Further, in a case where a distance to a physical object is short, the spray 60 sprays the cleansing agent at a low pressure.

It should be noted that the mode of spraying may include an amount of spraying of the cleansing agent, a direction of spraying of the cleansing agent, an orifice width of the spray nozzle 62, and the like. For example, in a case where a physical object is present in a large area, the spray 60 may spray the cleansing agent over a wide area with a larger orifice width of the spray nozzle 62. At this point in time, the spray 60 may spray the cleansing agent in larger amounts. Further, in a case where a physical object is present in a small area, the spray 60 may spray the cleansing agent over a narrow area with a smaller orifice width of the spray nozzle 62. At this point in time, the spray 60 may spray the cleansing agent in smaller amounts.

The operation button 70 is a physical button that serves as a trigger for at least either causing the light source 31 to emit light or causing the cleansing agent to be sprayed. For example, pressing the operation button 70 once causes excitation light to be emitted from the light source 31 and causes a physical object determination process to be performed. After that, pressing the operation button 70 once again causes the cleansing agent to be sprayed from the spray nozzle 62. Alternatively, a single depression of the operation button 70 may be a trigger for the emission of light from the light source 31, and the holding down of the operation button 70 may be a trigger for the spraying of the cleansing agent.

The operation button 70 may be integrated with the display 50. Specifically, the display 50 may be a touch panel display and may display a GUI (graphical user interface) object or the like for at least either causing the light source 31 to emit light or causing the cleansing agent to be sprayed. The user may, by touching the GUI object displayed on the display 50, at least either cause the light source 31 to emit light or cause the cleansing agent to be sprayed.

The range finder 80 measures a distance to a physical object. The range finder 80 measures a distance to a physical object, for example, by a ToF (time-of flight) method. Specifically, the range finder 80 includes a light source that emits light and a photodetector that receives a reflection of the emitted light by a physical object, and measures a distance to the physical object by measuring the time the emitted light takes to be received by the photodetector after being reflected by the physical object. The range finder 80 may employ either a phase-difference distance method or a pulse transmission method.

At least either the light source or the photodetector of the range finder 80 may serve also as at least either the light source 31 or the photodetector 32 of the optical sensor 30. Alternatively, the range finder 80 may be an ultrasonic sensor or an infrared sensor. Further, the range finder 80 may measure a distance to a physical object by a stereo camera method.

2. Determination Process Involving Use of Fluorescence Fingerprints

A determination process that the determination circuit 40 performs through the use of fluorescence fingerprints is described here.

Fluorescence fingerprints are excitation emission matrix (EEM) information. Fluorescence fingerprints are three-dimensional data based on three axes, namely excitation wavelength, fluorescence wavelength, and fluorescence intensity. The excitation wavelength is the wavelength of excitation light with which a physical object is irradiated. The fluorescence wavelength is the wavelength of fluorescence that is emitted from a physical object. Fluorescence fingerprints are obtained, for example, by measuring a fluorescence spectrum with continuous variations in the wavelength of excitation light with which a physical object is irradiated.

Each type of physical object has its own fluorescence fingerprints. That is, each type of physical object has its own combination of an excitation wavelength and a fluorescence wavelength at which a high fluorescence intensity is reached. For example, amino acids that form proteins, which are the basic constituents of food products or organisms, emit fluorescence with a peak at around 320 nm upon irradiation with excitation light with a peak at around 280 nm.

For this reason, for example, in Embodiment 1, the light source 31 emits excitation light with a peak, for example, at around 280 nm as the first light. The photodetector 32 receives light at an observed wavelength of, for example, around 320 nm. As a result, the signal strength of an electrical signal outputted from the optical sensor 30 represents the magnitude of fluorescence intensity. Accordingly, the determination circuit 40 can determine the presence or absence of an amino acid on the basis of the signal strength of the electrical signal.

By performing emission of excitation light and reception of light by the photodetector 32 with a plurality of combinations of an excitation wavelength and an observed wavelength, reception intensities for each separate combination can be obtained. This enables the signal processing circuit 41 to generate fluorescence fingerprints.

Figure 4:
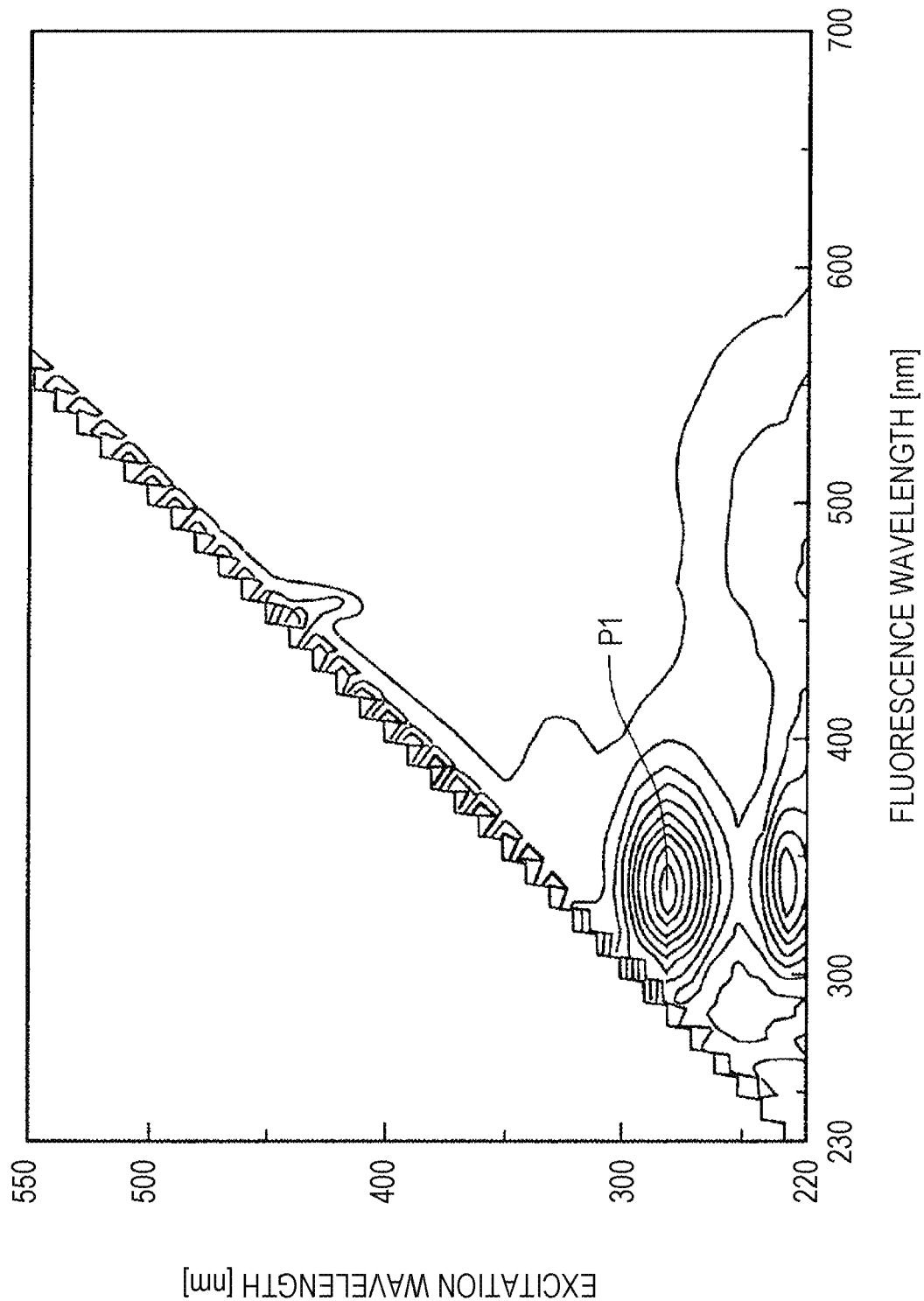
FIG. 4 is a diagram showing fluorescence fingerprints on a pixel in which a physical object is present, as acquired by the purifying apparatus according to Embodiment 1.

FIG. 4 is a diagram showing fluorescence fingerprints on a pixel in which a physical object is present, as acquired by the purifying apparatus 10 according to Embodiment 1. FIG. 4 shows two-dimensional coordinates whose vertical axis represents excitation wavelength and whose horizontal axis represents fluorescence wavelength and, on the two-dimensional coordinates, illustrates isointensity lines continuously connecting coordinates of equal signal strength.

The physical object used here is yoghurt adhering to a toilet tile and serving as a substitute for vomit or the like. For example, the light source 31 emits excitation light with time-continuous variations in the wavelength of the excitation light, and the photodetector 32 receives light with time-continuous variations in observed wavelength through the filters or the like. As a result, for each combination of an excitation wavelength and a fluorescence wavelength, an electrical signal representing a fluorescence intensity that corresponds to that combination is obtained. The fluorescence fingerprints shown in FIG. 4 are obtained by the signal processing circuit 41 processing electrical signals that are outputted from the photodetector 32.

As shown in FIG. 4, it is found that a peak P1 appeared in a position at an excitation wavelength of around 280 nm and a fluorescence wavelength of around 320 nm. Accordingly, it is found that fluorescence emitted from an amino acid contained in the yoghurt was detected.

In Embodiment 1, consideration is also given to light that is received by the photodetector 32 in a case where no physical object is present, as the determination circuit 40 determines the presence or absence of a physical object. Specifically, in a case where no physical object is present, reflected light or fluorescence from a floor surface or the like falling within the range of shooting by the photodetector 32 is received by the photodetector 32. For example, in the case of a toilet tile with yoghurt adhering thereto, fluorescence from the toilet tile can occur, too, as is the case with FIG. 4.

Figure 5:
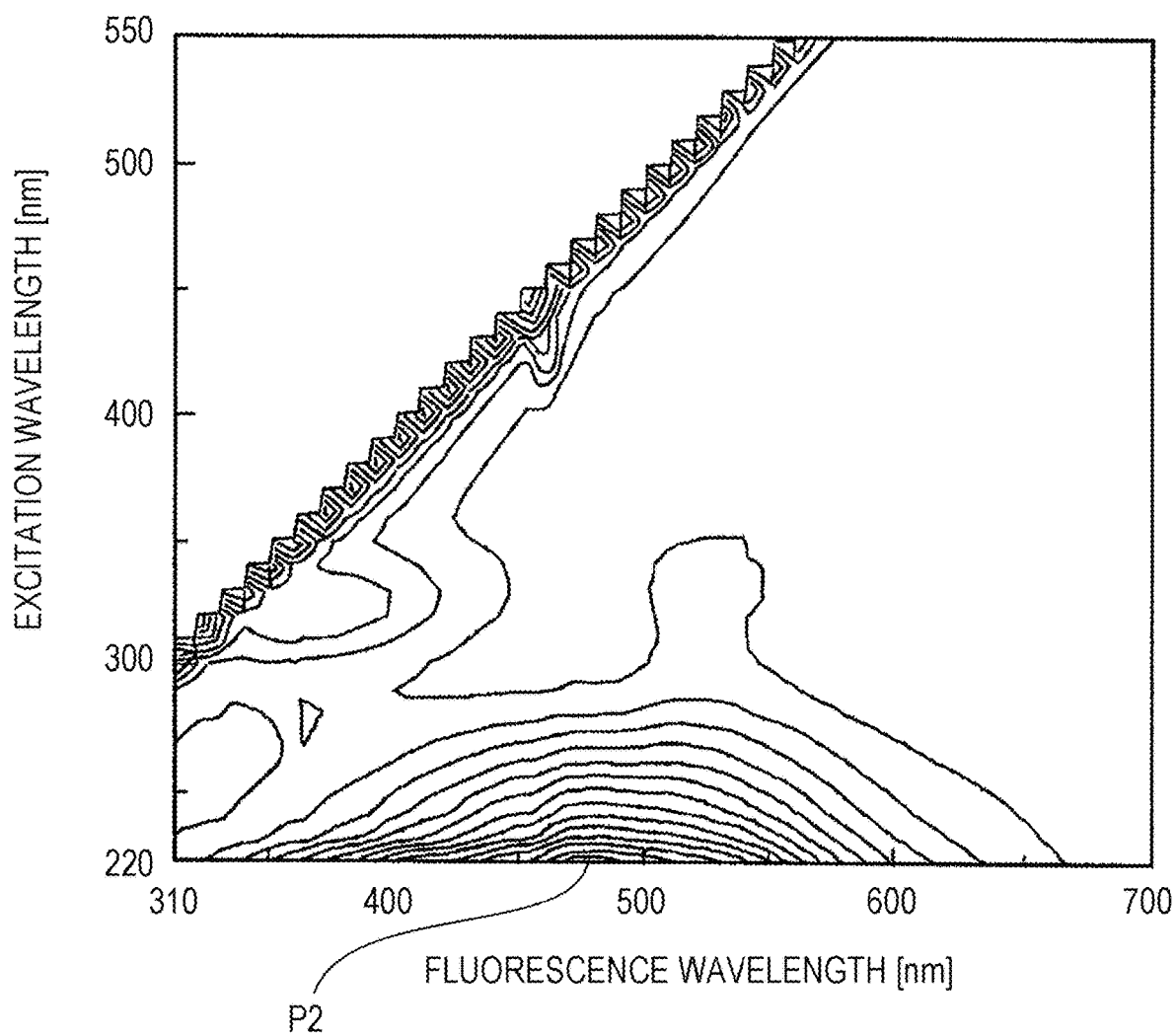
FIG. 5 is a diagram showing fluorescence fingerprints on a pixel in which no physical object is present, as acquired by the purifying apparatus according to Embodiment 1.

FIG. 5 is a diagram showing fluorescence fingerprints on a pixel in which no physical object is present, as acquired by the purifying apparatus 10 according to Embodiment 1. As is the case with FIG. 4, FIG. 5 shows two-dimensional coordinates whose vertical axis represents excitation wavelength and whose horizontal axis represents fluorescence wavelength and, on the two-dimensional coordinates, illustrates isointensity lines continuously connecting coordinates of equal signal strength.

FIG. 5 specifically shows the fluorescence fingerprints of a toilet tile. The fluorescence fingerprints of the toilet tile are generated by a method which is the same as that by which the fluorescence fingerprints shown in FIG. 4 are generated.

As shown in FIG. 5, it is found that a peak P2 appeared in a position at an excitation wavelength of around 220 nm and a fluorescence wavelength of around 480 nm. As can be seen from a comparison between FIG. 4 and FIG. 5, the toilet tile and an amino acid contained in the yoghurt have different combinations of an excitation wavelength and a fluorescence wavelength at which a high fluorescence intensity is reached. This makes it possible to detect the presence or absence of an amino acid without influence from fluorescence produced by the toilet tile.

Meanwhile, when no peak P2 is observed, it becomes possible to determine that a physical object other than an amino acid is adhering to the surface of the toilet tile, as the peak P2 appears in a case where nothing is adhering to the surface of the toilet tile. This also makes it possible to determine the presence or absence of a substance other than an amino acid to be detected.

3. Operation

Next, an operation of the purifying apparatus 10 according to Embodiment 1 is described.

Figure 6:
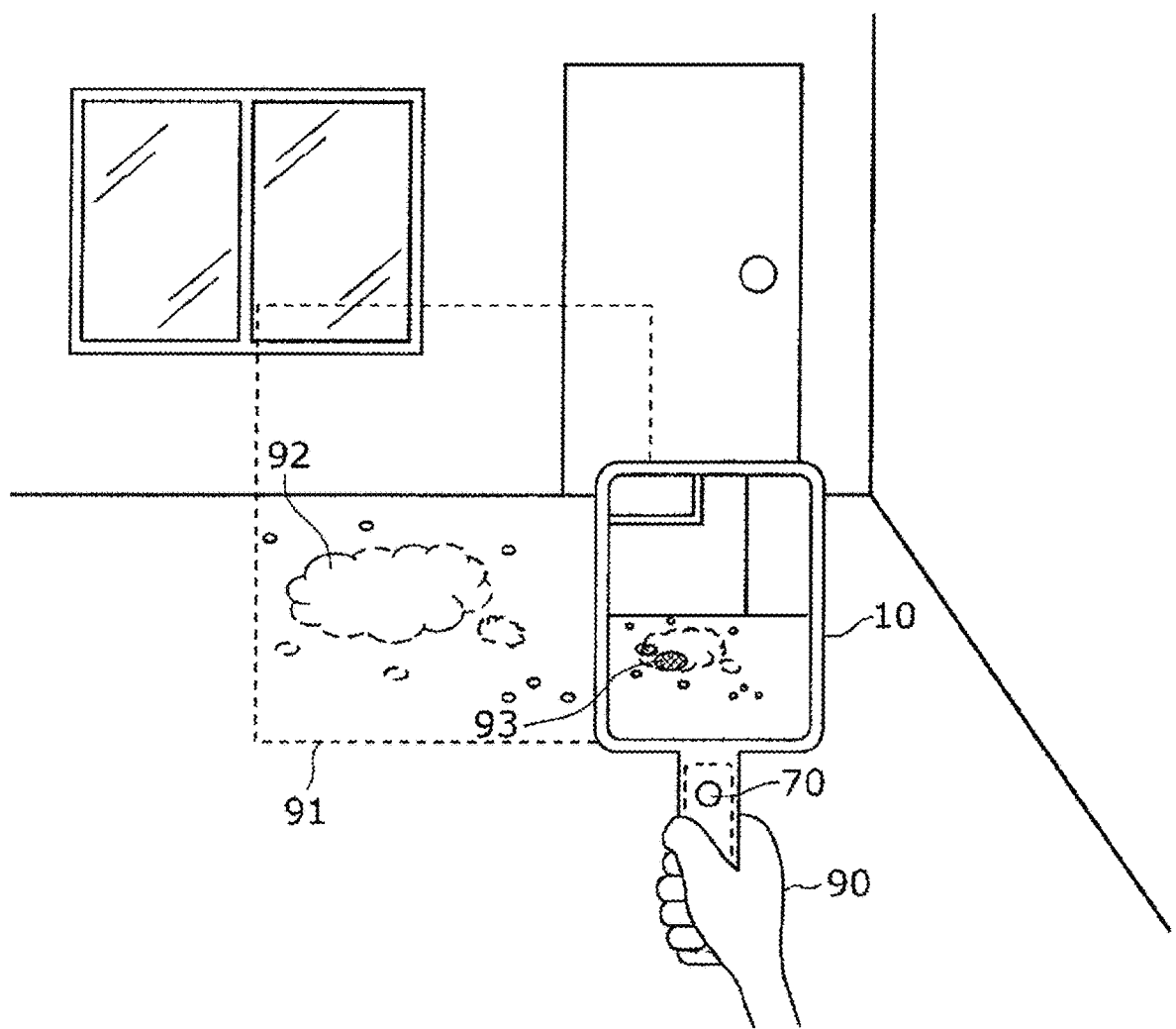
FIG. 6 is a diagram showing an example of use of the purifying apparatus according to Embodiment 1.
Figure 7:
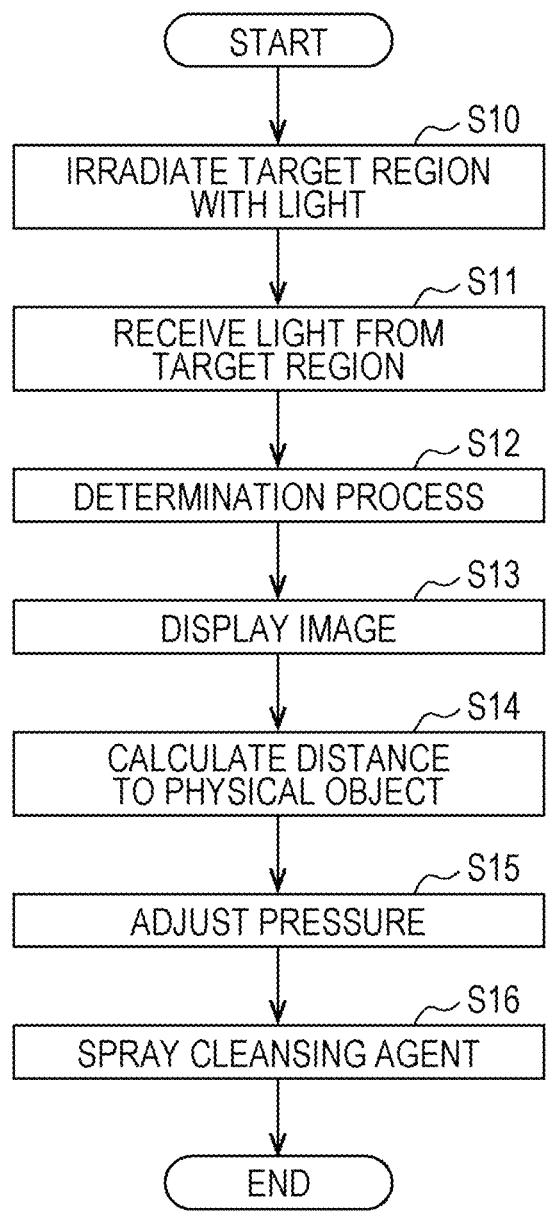
FIG. 7 is a flow chart showing an operation of the purifying apparatus according to Embodiment 1.

FIG. 6 is a diagram showing an example of use of the purifying apparatus 10 according to Embodiment 1. FIG. 7 is a flow chart showing an operation of the purifying apparatus 10 according to Embodiment 1.

In Embodiment 1, as shown in FIG. 6, the purifying apparatus 10 allows a user to freely change a target region 91 according to the user's intention by holding the handle 22 with one hand 90 of the user. For example, after having performed a cleaning process of removing vomit, the user uses the purifying apparatus 10 to check for a physical object 93, i.e. remnants of the vomit, with the target region 91 being an area including a cleaning trace 92 of the vomit. The target region 91 is equivalent to the region of photodetection (i.e. the range of shooting) by the photodetector 32. For example, the display 50 displays a shot image taken by the photodetector 32.

The user adjusts the attitude of the purifying apparatus 10 so that the cleaning trace 92 is included in a range of display on the display 50 of the purifying apparatus 10, i.e. the range of shooting by the photodetector 32, and depresses the operation button 70. Depression of the operation button 70 initiates an operation of the purifying apparatus 10.

First, as shown in FIG. 7, upon depression of the operation button 70, the light source 31 irradiates the target region 91 with excitation light as first light (S10). The photodetector 32 receives second light from the target region 91 irradiated with the first light from the light source (S11).

Figure 8:
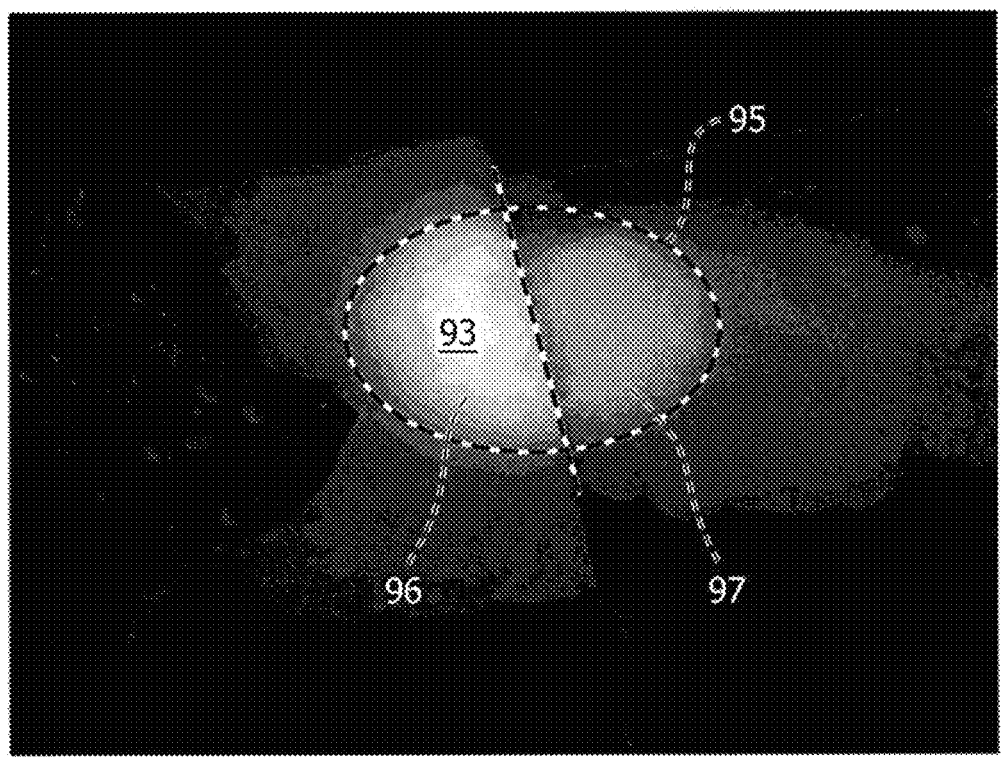
FIG. 8 is a diagram showing a raw image acquired by the purifying apparatus according to Embodiment 1.

Note here that FIG. 8 is a diagram showing a raw image acquired by the purifying apparatus 10 according to Embodiment 1. In FIG. 8, a region 95 being irradiated with the excitation light is surrounded by a dotted line. In the region 95, a toilet tile is present. Furthermore, the region 95 surrounded by the dotted line includes a left-side region 96 having yoghurt adhering thereto as the physical object 93 and a right-side region 97 having nothing adhering thereto.

As shown in FIG. 8, high-intensity light based on fluorescence is received from the left-side region 96, and low-intensity light based on a reflection of the excitation light is received from the right-side region 97.

Next, as shown in FIG. 7, the determination circuit 40 determines the presence or absence of the physical object 93 within the target region 91 (S12). In Embodiment 1, the excitation light that excites the physical object 93 is emitted as the first light; therefore, in a case where the physical object 93 is included in the target region 91, fluorescence from the physical object 93 is contained in the second light, which is received by the photodetector 32. Accordingly, the determination circuit 40 can determine that the physical object 93 is present in a pixel in which fluorescence from the physical object 93 has been detected. The determination circuit 40 determines the presence or absence of the physical object 93 for each pixel.

Figure 9:
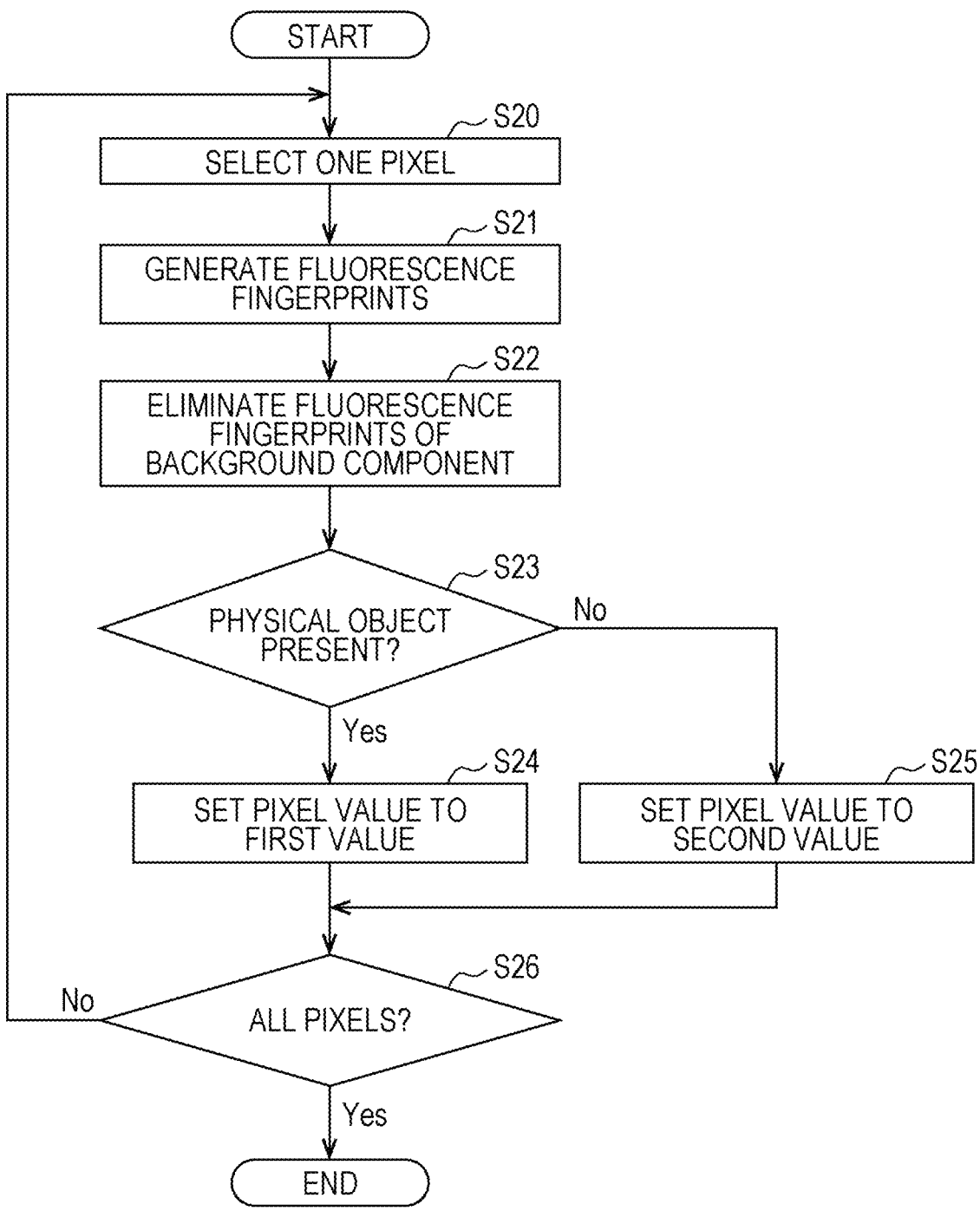
FIG. 9 is a flow chart showing an example of a determination process that is performed by a determination circuit of the purifying apparatus according to Embodiment 1.

Note here that FIG. 9 is a flow chart showing an example of a determination process that is performed by the determination circuit 40 of the purifying apparatus 10 according to Embodiment 1. First, as shown in FIG. 9, the determination circuit 40 selects one pixel (S20). Next, the determination circuit 40 generates fluorescence fingerprints on the basis of an electrical signal outputted from the pixel thus selected (S21). Next, the determination circuit 40 eliminates the fluorescence fingerprints of a background component from the fluorescence fingerprints thus generated (S22). For example, the determination circuit 40 subtracts the fluorescence fingerprints of the background component from the fluorescence fingerprints thus generated. The fluorescence fingerprints of the background component are specifically the fluorescence fingerprints of flooring included in the range of shooting, and are ones generated in advance in a case where it is clear that the physical object 93 is not present.

Next, the determination circuit 40 determines, on the basis of the fluorescence fingerprints subjected to the subtraction, the presence or absence of the physical object 93 in the pixel thus selected (S23). For example, the determination circuit 40 determines whether the fluorescence intensity of a combination that is equivalent to an amino acid, or specifically, a combination of an excitation wavelength of around 280 nm and a fluorescence wavelength of around 320 nm is not lower than a predetermined threshold. In a case where the fluorescence intensity of the combination is not lower than the threshold, the determination circuit 40 determines that the physical object 93 is present. In a case where the fluorescence intensity of the combination is lower than the threshold, the determination circuit 40 determines that the physical object 93 is not present.

In a case where the physical object 93 is present (Yes in S23), the determination circuit 40 sets the pixel value of the pixel thus selected to a first value (S24). The first value is for example the maximum pixel value. In a case where the physical object 93 is not present (No in S23), the determination circuit 40 sets the pixel value of the pixel thus selected to a second value (S25). The second value is a value that is different from the first value and, for example, is the minimum pixel value.

From then on, steps S20 to S25 are repeated until completion of processing of all pixels (No in S26). This enables the determination circuit 40 to binarize a shot image according to the presence or absence of the physical object 93.

Performing the determination process determines that the physical object 93 is present in the left-side region 96 and not present in the right-side region 97 in FIG. 8. In performing the determination process, compression of information may be performed. Fluorescence fingerprints, which are three-dimensional data, contain a large amount of information and may take a long time to be processed. For this reason, the time required for the determination process may be reduced by reducing throughput, for example, by performing a pixel interpolation process or other processes. That is, in step S26 shown in FIG. 9, the process does not need to be performed on all pixels.

Figure 10:
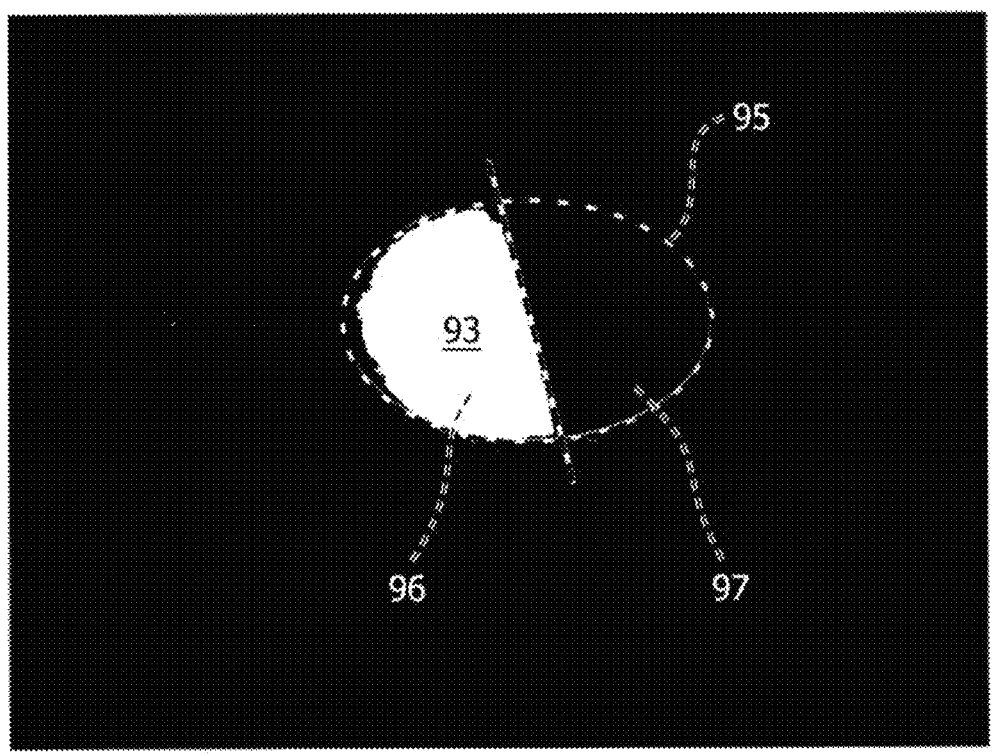
FIG. 10 is a diagram showing an image representing a determination result generated by the purifying apparatus according to Embodiment 1.

FIG. 10 is a diagram showing an image representing a determination result generated by the purifying apparatus 10 according to Embodiment 1. For example, the signal processing circuit 41 binarizes a pixel in which the physical object 93 has been determined to be present and a pixel in which the physical object 93 is not present, whereby the image shown in FIG. 10 is generated. As shown in FIG. 7, after completion of the determination process (S12), the display 50 displays, as the determination result, the image shown in FIG. 10 (S13).

The image shown in FIG. 10 may be displayed while overlapping an image generated on the basis of visible light. This makes it possible to comprehensively display the position of the physical object 93 in a real space.

Next, the range finder 80 calculates a distance to the physical object 93 thus detected (S14). Specifically, the range finder 80 emits infrared light toward the physical object 93 and receives a reflection of the infrared light, thereby calculating the distance on the basis of the time from emission to reception.

Next, the spray 60 adjusts the pressure of spraying of the cleansing agent on the basis of the distance thus calculated (S15). Specifically, the longer the distance thus calculated is, the higher the spray 60 makes the pressure, and the shorter the distance thus calculated is, the lower the spray 60 makes the pressure. Further, at this point in time, the spray 60 may adjust the direction of spraying of the cleansing agent on the basis of the position of the physical object 93 thus detected. For example, as shown in FIG. 10, the direction of spraying may be pointed leftward in a case where, as shown in FIG. 10, the physical object 93 has been detected in the left-side region in the image.

Finally, the spray 60 sprays the cleansing agent, stored in the container 61, at a predetermined pressure through the spray nozzle 62 (S16). This brings the cleansing agent thus sprayed into contact with the physical object 93 thus detected and can render the physical object 93 harmless by degrading it.

It should be noted that the distance calculation (S14) and the pressure adjustment (S15) may precede the image display (S13).

Figure 11:
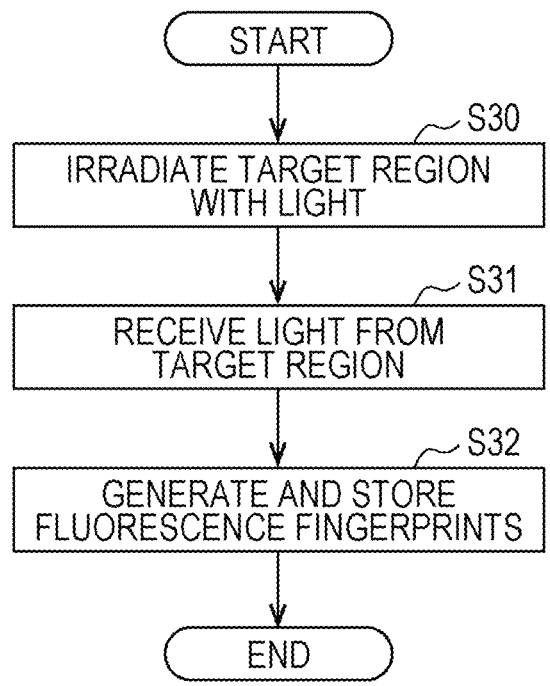
FIG. 11 is a flow chart showing preprocessing of the purifying apparatus according to Embodiment 1.

Further, in Embodiment 1, the accuracy of determination is increased by acquiring fluorescence fingerprints in advance in a case where it is clear that the physical object 93 is not present. FIG. 11 is a flow chart showing preprocessing of the purifying apparatus 10 according to Embodiment 1.

For example, in a case where the operation button 70 has been depressed, the light source 31 irradiates the target region 91 with the excitation light as the first light (S30). The photodetector 32 receives the second light from the target region 91 irradiated with the first light from the light source 31 (S31).

The determination circuit 40 generates fluorescence fingerprints for each combination of an excitation wavelength and a fluorescence wavelength as the fluorescence fingerprints of a case where the physical object 93 is not present and stores the fluorescence fingerprints thus generated in a memory or the like as the fluorescence fingerprints of the background component (S32).

The fluorescence fingerprints of the background component stored in the memory or the like is utilized as reference information in the determination process (S12 and FIG. 7). This makes it possible to reduce the influence of the background component such as the toilet tile or the flooring and increase the accuracy of detection of the physical object 93.

4. CONCLUSION

As noted above, the optical sensor 30, determination circuit 40, display 50, spray 60, operation button 70, and range finder 80 of the purifying apparatus 10 according to Embodiment 1 are housed in the housing 20 or retained by the housing 20. In this way, the purifying apparatus 10, which is integrated by the single housing 20, makes it possible to perform a simple operation starting with detection of the physical object 93 and ending with removal of the physical object 93. Further, the handle 22 of the housing 20 makes it possible to easily carry around the purifying apparatus 10. This makes it possible to determine the presence or absence of the physical object 93 in various places.

MODIFICATIONS

The following describes modifications of Embodiment 1 described above. It should be noted that the following modifications give a description with a focus on differences from Embodiment 1 and omit or simplify a description of common features.

Modification 1

First, a modification of the determination process is described. In Embodiment 1, an example has been described in which the presence or absence of a physical object is determined through the use of fluorescence fingerprints. In Modification 1 of Embodiment 1, on the other hand, a determination of a physical object is made on the basis of a comparison between a reception intensity and a threshold.

For example, in a case where the region 95 including the physical object 93 has been irradiated with excitation light as is the case with the shot image shown in FIG. 8, fluorescence is emitted from the physical object 93, while no fluorescence is emitted from the region 97, in which the physical object 93 is not present. For this reason, of the plurality of pixels of the photodetector 32, those pixels in which the physical object 93 is present receive high-intensity second light containing fluorescence, and those pixels in which the physical object 93 is not present receive second light containing no fluorescence. That is, there are differences in the intensity of light among the pixels, depending on the presence or absence of the physical object 93.

To address this problem, the determination circuit 40 according to Modification 1 of Embodiment 1 determines the presence or absence of the physical object 93 on the basis of a result of a comparison between the reception intensity of the second light and a predetermined threshold. The reception intensity of the second light is expressed by a pixel value of a shot image. The threshold is defined on the basis of a reception intensity or the like acquired in advance in a case where it is clear that the physical object 93 is not present.

Specifically, the determination circuit 40 chooses, as the threshold, the reception intensity of light from the region 95 irradiated with the excitation light in a case where the physical object 93 is not present. For example, the average of reception intensities of the region 97 serves as the threshold.

Alternatively, the threshold may be smaller than the average of reception intensities of the region 97. In this case, there is a possibility that a mistaken determination of the presence of the physical object 93 might be made even as to a pixel in which the physical object 93 is not present. However, this is sufficient for the purpose of removing the physical object 93, as a pixel in which the physical object 93 is present can be substantially surely determined.

Figure 12:
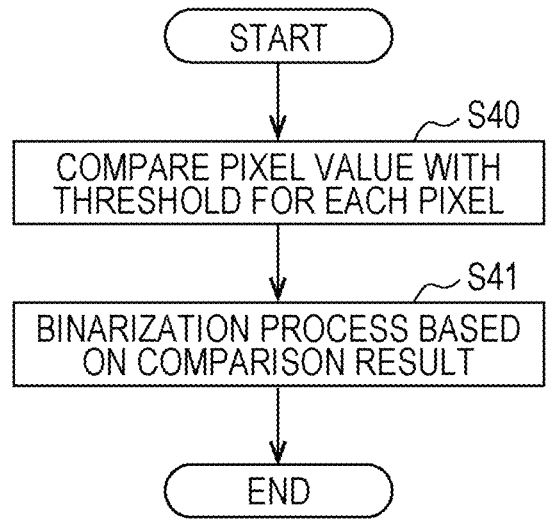
FIG. 12 is a flow chart showing an example of a determination process that is performed by a determination circuit of a purifying apparatus according to Modification 1 of Embodiment 1.

An operation of the purifying apparatus 10 according to Modification 1 of Embodiment 1 is the same as that of Embodiment 1, except that the determination process (S12 of FIG. 7) is different. FIG. 12 is a flow chart showing an example of a determination process that is performed by the purifying apparatus 10 according to Modification 1 of Embodiment 1.

As shown in FIG. 12, the determination circuit 40 according to Modification 1 of Embodiment 1 compares a pixel value with the threshold for each pixel (S40). The determination circuit 40 performs a binarization process on a short image on the basis of a comparison result (S41). Specifically, in a case where the pixel value is not smaller than the threshold, the determination circuit 40 sets the pixel value to the first value, and in a case where the pixel value is smaller than the threshold, the determination circuit 40 sets the pixel value to the second value. The binarization process (S41) is the same as steps S24 and S25 shown in FIG. 9.

Figure 13:
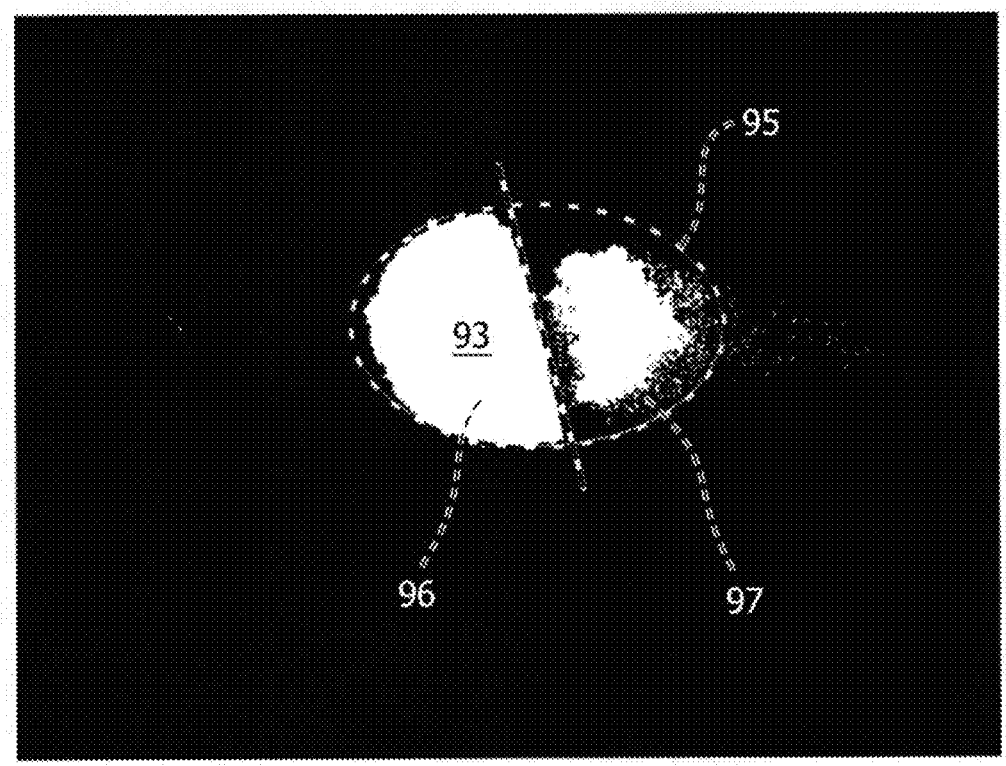
FIG. 13 is a diagram showing an image representing a determination result generated by the purifying apparatus according to Modification 1 of Embodiment 1.

FIG. 13 is a diagram showing an image representing a determination result generated by the purifying apparatus 10 according to Modification 1 of Embodiment 1. FIG. 13 shows a case where the threshold is a value that is smaller than the average of reception intensities of the region 97. For example, the signal processing circuit 41 generates the image shown in FIG. 13 by binarizing the shot image shown in FIG. 8 on the basis of the threshold.

As shown in FIG. 13, it is found that even in the region 97, in which the physical object 93 is not supposed to be present, white pixels are contained and the physical object 93 is determined to be present. Meanwhile, in the region 96, too, the physical object 93 is determined to be present.

In this case, the spray 60 sprays the cleansing agent over the region 97 as well as the region 96. No particular use is made of the cleansing agent sprayed over the region 97, as the physical object 93 is not present in the region 97; however, the physical object 93 can be removed by the cleansing agent sprayed over the region 96.

As noted above, the purifying apparatus 10 according to Modification 1 of Embodiment 1 makes it possible to determine the presence or absence of the physical object 93 by binarizing a shot image, thus making it possible to reduce throughput and time required for determination.

In Modification 1 of Embodiment 1, in which there is no need to generate fluorescence fingerprints, the light source 31 needs only emit a single ray of excitation light as the first light. Similarly, the photodetector 32 needs only receive the second light across a reception band corresponding to a single wavelength or the entire band. This makes it possible to simplify the configuration of the optical sensor 30 as well as the configuration of the determination circuit 40. This makes it possible to achieve reductions in size and weight of the purifying apparatus 10.

Modification 2

Next, another modification of the determination process is described. In Modification 2 of Embodiment 1, a determination of a physical object is made on the basis of the fact that fluorescence is light that is longer in wavelength than excitation light.

The determination circuit 40 according to Modification 2 of Embodiment 1 determines the presence or absence of a physical object on the basis of a component contained in the second light that is longer in wavelength than the first light. As described in Modification 1 of Embodiment 1, the second light contains a reflection of the excitation light. For this reason, the accuracy of detection of a physical object can be further increased by eliminating a component of the excitation light from the light to be received.

Figure 14:
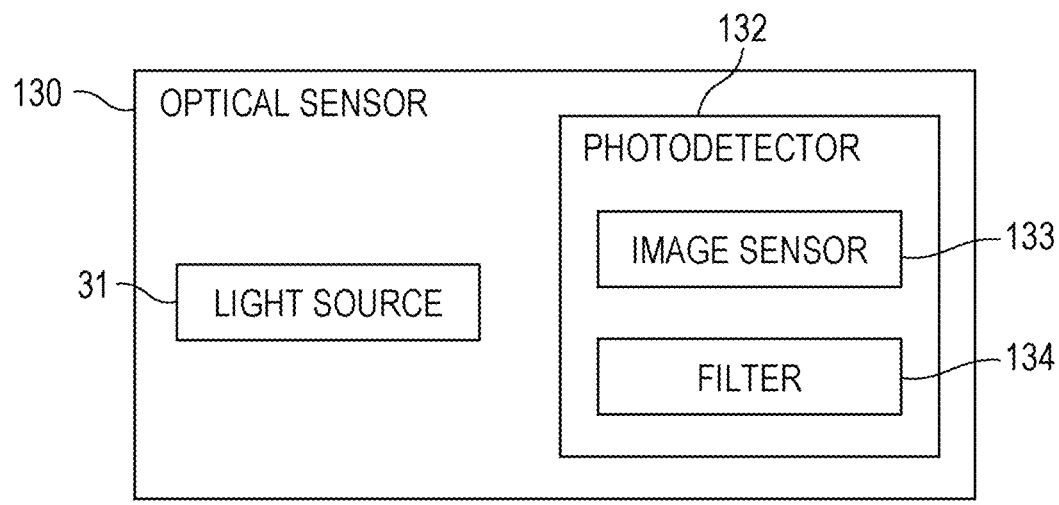
FIG. 14 is a block diagram showing a configuration of an optical sensor of a purifying apparatus according to Modification 2 of Embodiment 1.

FIG. 14 is a block diagram showing a configuration of an optical sensor 130 of the purifying apparatus 10 according to Modification 2 of Embodiment 1. As shown in FIG. 14, the optical sensor 130 differs from the optical sensor 30 according to Embodiment 1 in that the optical sensor 130 includes a photodetector 132 instead of the photodetector 32.

The photodetector 132 includes an image sensor 133 and a filter 134. As in the case of Embodiment 1, the image sensor 133 is an image sensor having a plurality of pixels arrayed in a two-dimensional state.

The filter 134 is a filter that blocks the first light emitted by the light source 31 and transmits light of a component that is longer in wavelength than the first light. For example, the filter 134 blocks a wavelength component of 300 nm or shorter and transmits light of a wavelength component of longer than 300 nm.

An operation of the purifying apparatus 10 according to Modification 2 of Embodiment 1 is the same as that of the purifying apparatus 10 according to Modification 1 of Embodiment 1. Specifically, the determination circuit 40 of the purifying apparatus 10 according to Modification 2 of Embodiment 1 performs a determination process along with the flow chart shown in FIG. 12.

At this point in time, the threshold for use in comparison with a pixel value may be smaller than the threshold for use in Modification 1 of Embodiment 1. The elimination of the wavelength component of the excitation light by the filter 134 makes it possible to reduce the influence of the reflection of the excitation light even when the threshold is small. Making the threshold smaller makes it possible to detect low-intensity fluorescence from the physical object 93, thus making it possible to increase the accuracy of detection of the physical object 93.

In Modification 2 of Embodiment 1, in which there is no need to generate fluorescence fingerprints, the light source 31 needs only emit a single ray of excitation light as the first light, as is the case with Modification 1 of Embodiment 1. Similarly, the photodetector 32 needs only receive the second light across a reception band corresponding to a single wavelength or the entire band. This makes it possible to simplify the configuration of the optical sensor 130 as well as the configuration of the determination circuit 40. This makes it possible to achieve reductions in size and weight of the purifying apparatus 10.

Modification 3

Next, a modification of Embodiment 1 is described. Modification 3 of Embodiment 1 determines the mode of spraying of the cleansing agent in consideration of a tilt of the purifying apparatus as well as a distance to a physical object.

Figure 15:
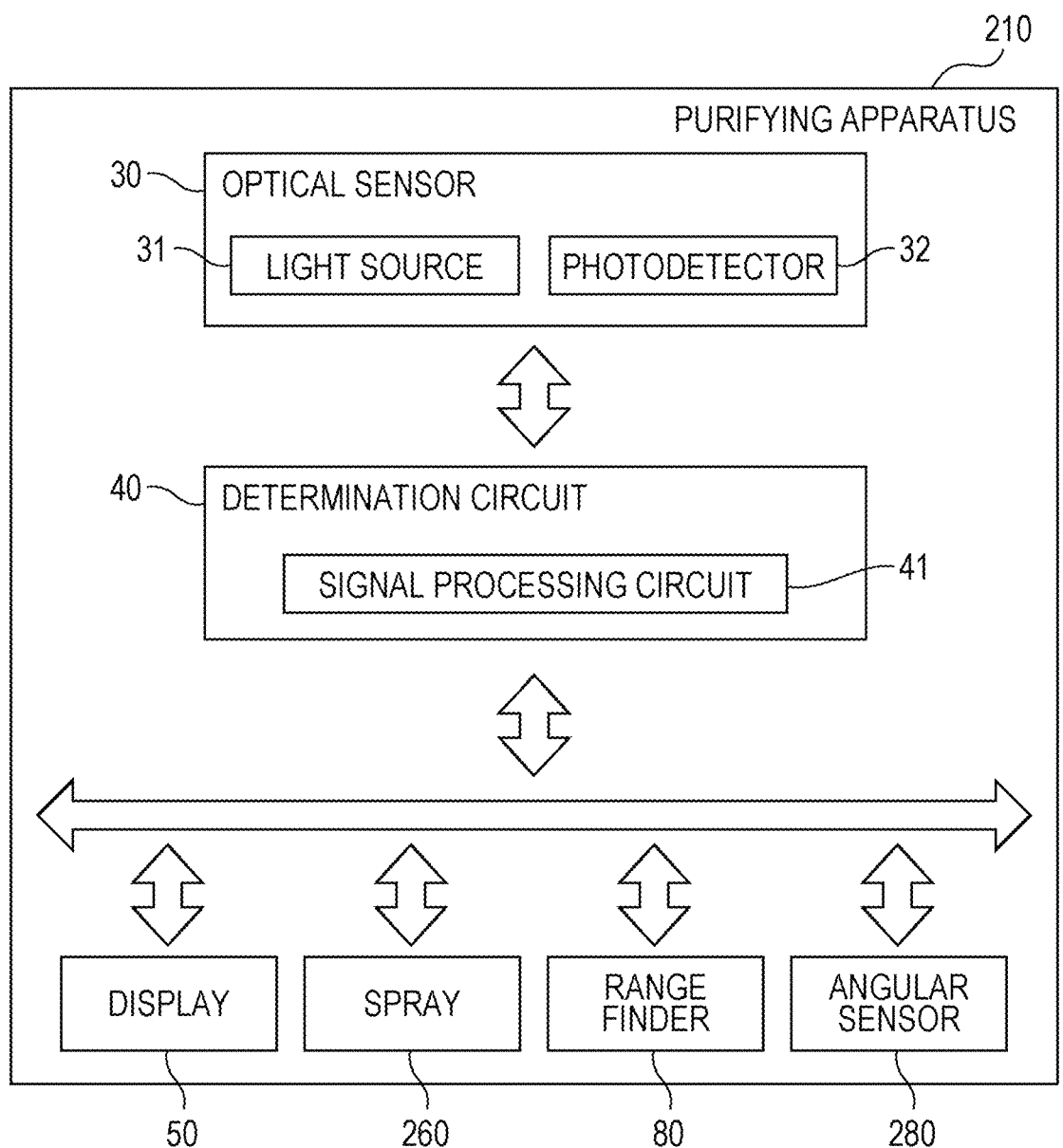
FIG. 15 is a block diagram showing a configuration of a purifying apparatus according to Modification 3 of Embodiment 1.

FIG. 15 is a block diagram showing a configuration of a purifying apparatus 210 according to Modification 3 of Embodiment 1. As shown in FIG. 15, the purifying apparatus 210 differs from the purifying apparatus 10 according to Embodiment 1 in that the purifying apparatus 210 further includes an angular sensor 280 and includes a spray 260 instead of the spray 60.

The angular sensor 280 detects the tilt of the purifying apparatus 210. The tilt is expressed by an angle with respect to a horizontal plane or a vertical direction. The angular sensor 280 is achieved by at least one of an acceleration sensor, an angular velocity sensor, a geomagnetic sensor, and a capacitance sensor.

As is the case with the spray 60, the spray 260 includes a container 61 and a spray nozzle 62. The spray 260 controls the mode of spraying of the cleansing agent according to a distance measured by the range finder 80 and a tilt detected by the angular sensor 280.

Specifically, the spray 260 determines the direction of spraying of the cleansing agent on the basis of the tilt detected by the angular sensor 280. The direction of spraying of the cleansing agent is determined by the orientation of the spray 62 and a direction from the spray 62 toward the physical object 93.

A flying distance of the cleansing agent greatly varies under the influence of gravity. For example, in a case where the physical object 93 is present on a ceiling surface or the like, the cleansing agent is sprayed in an upward direction or a vertically upward direction. At this point in time, the cleansing agent needs to be sprayed at a high pressure in order to reach the physical object 93.

On the other hand, in a case where the physical object 93 is present directly below the purifying apparatus 210, even a low pressure makes it easy for the cleaning agent to gravitationally reach the physical object 93, as the cleansing agent is sprayed in a vertically downward direction.

Take as an example a case of the same distance to the physical object 93. In a case where the direction of spraying of the cleansing agent points toward a higher position than the horizontal plane, the spray 260 sprays the cleansing agent at a higher pressure than in a case where the direction of spraying is parallel to the horizontal plane. The closer the direction of spraying becomes to the vertically upward direction, the higher the spray 260 makes the spraying pressure. Further, in a case where the direction of spraying of the cleansing agent points toward a lower position the horizontal plane, the spray 260 sprays the cleansing agent at a lower pressure than in a case where the direction of spraying is parallel to the horizontal plane. The closer the direction of spraying becomes to the vertically downward direction, the lower the spray 260 makes the spraying pressure.

In Modification 3 of Embodiment 1, the spray 260 has stored in a memory or the like a table of association of pressures of spraying of the cleansing agent with combinations of a tilt of the purifying apparatus 210 and a distance to the physical object 93. The spray 260 determines a pressure from a tilt and a distance with reference to the table and sprays the cleansing agent at the pressure thus determined.

As noted above, the purifying apparatus 210 according to Modification 3 of Embodiment 1 makes it possible to further increase the probability of contact between the cleansing agent and a physical object, thus making it possible to further efficiently remove the physical object.

Embodiment 2

Next, Embodiment 2 is described. The following description gives a description with a focus on differences from Embodiment 1, its modifications, and the like and omit or simplify a description of common features.

Figure 16:
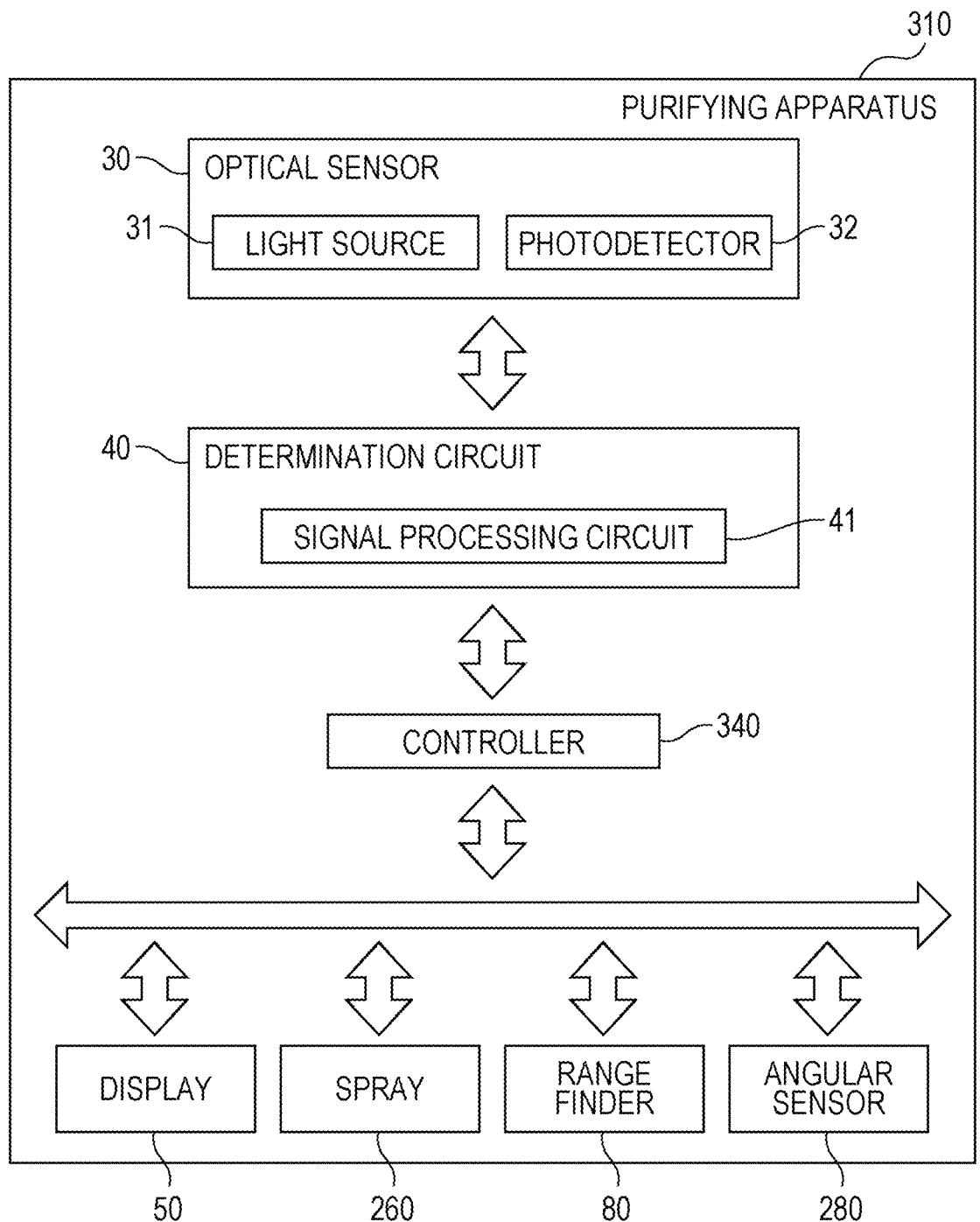
FIG. 16 is a block diagram showing a configuration of a purifying apparatus according to Embodiment 2.

FIG. 16 is a block diagram showing a configuration of a purifying apparatus 310 according to Embodiment 2. As shown in FIG. 16, the purifying apparatus 310 differs from the purifying apparatus 210 according to Modification 3 of Embodiment 1 in that the purifying apparatus 310 further includes a controller 340.

The controller 340 is for example a microcomputer. The controller 340 is achieved, for example, by a nonvolatile memory in which a program is stored, a volatile memory serving as a transitory recording region in which to execute the program, an I/O port, a processor that executes the program, or other components. A function that the controller 340 executes may be achieved by software that is executed by the processor or may be achieved by a dedicated electronic circuit including a plurality of circuit elements. Further, the controller 340 and the determination circuit 40 may share hardware resources such as memories with each other.

The controller 340 controls, on the basis of a distance measured by the range finder 80, how the spray 260 sprays the cleansing agent. Specifically, the controller 340 controls, according to at least either a combination of a distance measured by the range finder 80 and a pressure at which the spray 260 sprays the cleansing agent or a combination of a distance measured by the range finder 80 and a tilt of the spray nozzle 62, conditions under which the cleansing agent is sprayed.

For example, the controller 340 determines, according to a combination of a distance measured by the range finder 80 and a tilt of the spray nozzle 62, a pressure at which the spray 260 sprays the cleansing agent. Specifically, when a tilt pointing toward a lower position than an imaginary plane that is perpendicular to the direction of gravitational force, i.e. the horizontal plane, has been detected, the controller 340 calculates a first pressure that allows the cleansing agent to reach the physical object 93, and then the controller 340 causes the cleansing agent to be sprayed trough the spray nozzle 62 at the first pressure thus calculated. Specifically, the controller 340 calculates the first pressure according to Eq. (7), which will be described later. Alternatively, when a tilt pointing toward a higher position than the horizontal plane has been detected, the controller 340 calculates a second pressure that is higher than the first pressure, and then the controller 340 causes the cleansing agent to be sprayed trough the spray nozzle 62 at the second pressure thus calculated. Specifically, the controller 340 calculates the second pressure according to Eq. (12), which will be described later.

Next, a specific method for calculating a pressure at which the cleansing agent is sprayed is described. First, methods for measuring a distance from the spray nozzle 62 to the physical object 93 and detecting a tilt of the spray nozzle 62 during ranging are described with reference to FIGS. 17, 18A, and 18B.

Figure 17:
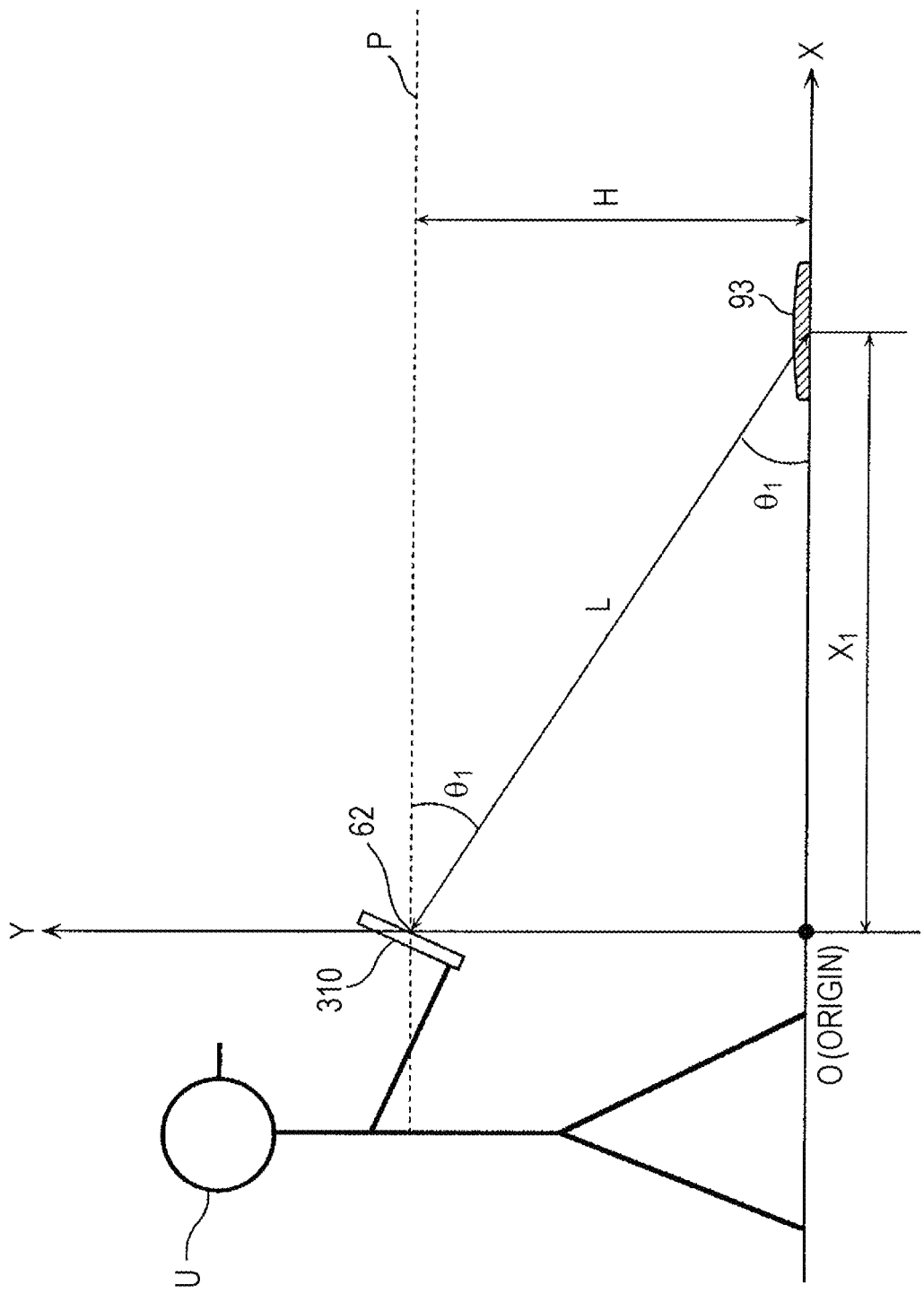
FIG. 17 is a schematic view showing a positional relationship between the purifying apparatus according to Embodiment 2 and a physical object during ranging.

FIG. 17 is a schematic view showing a positional relationship between the purifying apparatus 310 according to Embodiment 2 and a physical object 93 during ranging. Specifically, FIG. 17 is a side view of a user U holding the purifying apparatus 310 and the physical object 93 from the side.

In FIG. 17, the X axis and the Y axis are two axes that are orthogonal to each other. The X axis is parallel to a horizontal direction. The Y axis is parallel to a vertical direction, i.e. the direction of gravitational force. Further, FIG. 17 shows as an example a case where the physical object 93 has been detected on a floor surface by the determination circuit 40. The dotted line shown in FIG. 17 indicates an imaginary plane P that is perpendicular to the direction of gravitational force. The same applies to FIGS. 19 and 20, which will be described later.

The distance "L", shown in FIG. 17, is a direct distance from the spray nozzle 62 to the physical object 93. The distance L is measured by the range finder 80.

The angle of inclination "$\theta_1$" represents the tilt of the spray nozzle 62 with respect to the imaginary plane P. Specifically, the angle of inclination $\theta_1$ is an angle that the central axis of the spray nozzle 62 forms with respect to the imaginary plane P. The central axis of the spray nozzle 62 coincides with the direction of spraying. The angle of inclination $\theta_1$ is detected by the angular sensor 280.

The horizontal distance "$X_1$" is a distance between the spray nozzle 62 and the physical object 93 along a horizontal direction. The height "H" is a distance between the spray nozzle 62 and the physical object 93 along a perpendicular direction. The height H takes on a positive value in a case where the spray nozzle 62 is higher than the physical object 93 and takes on a negative value in a case where the spray nozzle 62 is lower than the physical object 93.

In Embodiment 2, the central axis of the spray nozzle 62, the optical axis of the photodetector 32, and the optical axis of the range finder 80 are parallel to one another. For this reason, the angle of inclination $\theta_1$ of the spray nozzle 62 during ranging substantially coincides with an angle that the ranging direction forms with respect to the imaginary plane P. Further, since the physical object 93 is several tens of centimeters to several meters away from the purifying apparatus 310, the spray nozzle 62, the photodetector 32, and the range finder 80 can be deemed to be at substantially the same position.

For this reason, the tilt of the spray nozzle 62 during ranging substantially coincides with the direction from the spray nozzle 62 toward the physical object 93, i.e. a tilt that the ranging direction forms with respect to the imaginary plane P. Accordingly, the horizontal distance $X_1$ and the height H are expressed by Eq. (1) and Eq. (2), respectively, as follows:

$$X_1 = L \cos \theta_1 \tag{1}$$

$$H = L \sin \theta_1 \tag{2}$$

In Embodiment 2, the controller 340 calculates the horizontal distance $X_1$ and the height H according to Eq. (1) and Eq. (2), respectively, on the basis of the distance L measured by the range finder 80 and the angle of inclination $\theta_1$ of the spray nozzle 62 during ranging. Alternatively, the controller 340 may correct the distance L and the angle of inclination $\theta_1$ thus measured on the basis of differences in inclination and position among the axes of the spray nozzle 62, the photodetector 32, and the range finder 80 and calculate the horizontal distance $X_1$ and the height H on the basis of the distance L and the angle of inclination $\theta_1$ thus corrected.

Figure 18A:
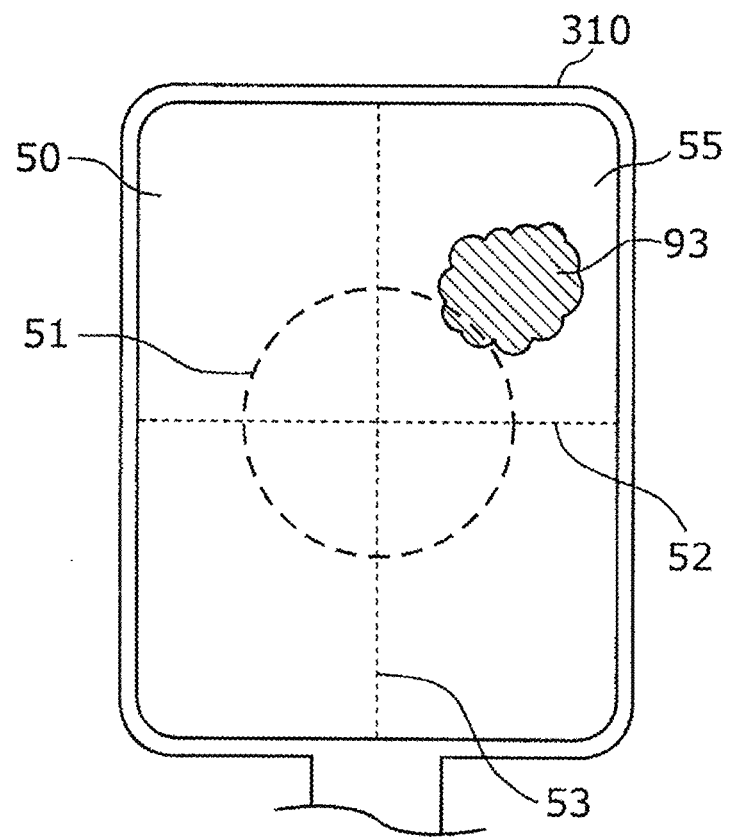
FIG. 18A is a diagram showing an example of a screen that is displayed on a display during ranging of the purifying apparatus according to Embodiment 2.
Figure 18B:
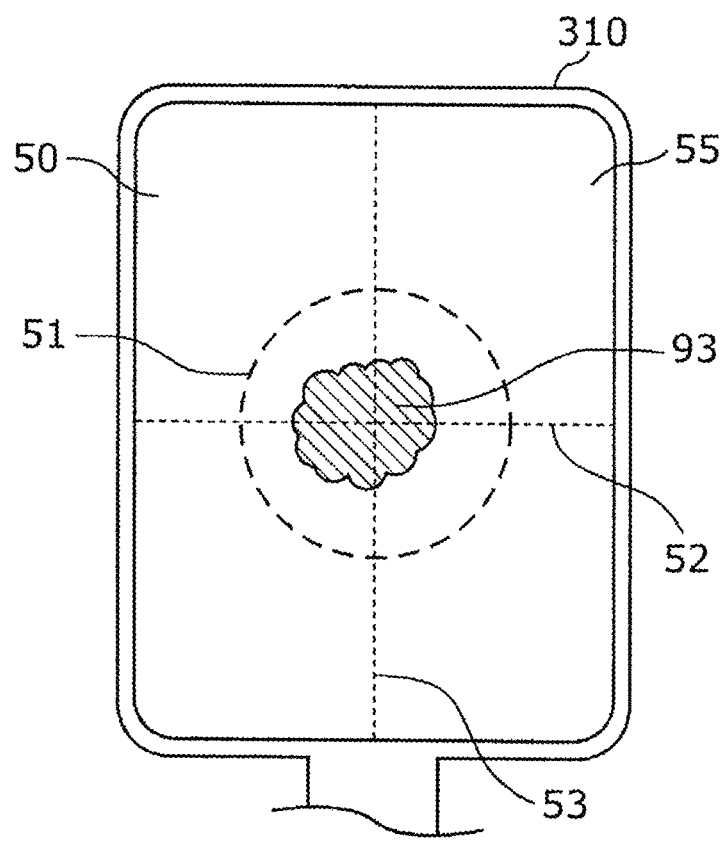
FIG. 18B is a diagram showing an example of a screen that is displayed on the display during ranging of the purifying apparatus according to Embodiment 2.

FIGS. 18A and 18B are each a diagram showing an example of a screen that is displayed on the display 50 during ranging of the purifying apparatus 310 according to Embodiment 2. As shown in FIGS. 18A and 18B, the display 50 displays a shot image 55 generated by the photodetector 32. The shot image 55 includes a physical object 93 determined by the determination circuit 40. Instead of the shot image 55, an image generated by the determination circuit 40, such as the image shown in FIG. 10, may be displayed on the display 50.

The display 50 of the purifying apparatus 310 displays a so-called water level. Specifically, as shown in FIG. 18A, the display 50 displays a circular frame 51, a horizontal line 52, and a perpendicular line 53. The circular frame 51 is a circle centered at a point of intersection between the horizontal line 52 and the perpendicular line 53. The point of intersection between the horizontal line 52 and the perpendicular line 53 is located, for example, in the center of the screen of the display 50.

The circular frame 51, the horizontal line 52, and the perpendicular line 53 are all displayed to assist the user U in positioning the physical object 93. For example, the user U watches the display 50 to adjust the tilt of the purifying apparatus 310 so that at least a portion of the physical object 93 falls within the circular frame 51. Alternatively, the user U watches the display 50 to adjust the tilt of the purifying apparatus 310 so that at least a portion of the physical object 93 coincides with the point of intersection between the horizontal line 52 and the perpendicular line 53. At least one of the circular frame 51, the horizontal line 52, and the perpendicular line 53 does not need to be displayed.

When at least a portion of the physical object 93 falls within the circular frame 51 or coincides with the point of intersection between the horizontal line 52 and the perpendicular line 53 as shown in FIG. 18B, the user U gives a ranging or tilt detection instruction by operating the operation button 70 or the like. Upon receiving the instruction, the controller 340 causes the range finder 80 to measure the display L to the physical object 93 and causes the angular sensor 280 to detect the tilt of the spray nozzle 62. Alternatively, upon detecting that at least a portion of the physical object 93 falls within the circular frame 51 or coincides with the point of intersection between the horizontal line 52 and the perpendicular line 53, the controller 340 may cause ranging and tilt detection to be performed.

In Embodiment 2, the tilt of the spray nozzle 62 during spraying of the cleansing agent is determined by the user U. The controller 340 calculates, according to the tilt thus determined, a pressure at which the cleansing agent is sprayed. In the following, a specific method for calculating a pressure is described with reference to FIGS. 19 and 20.

Figure 19:
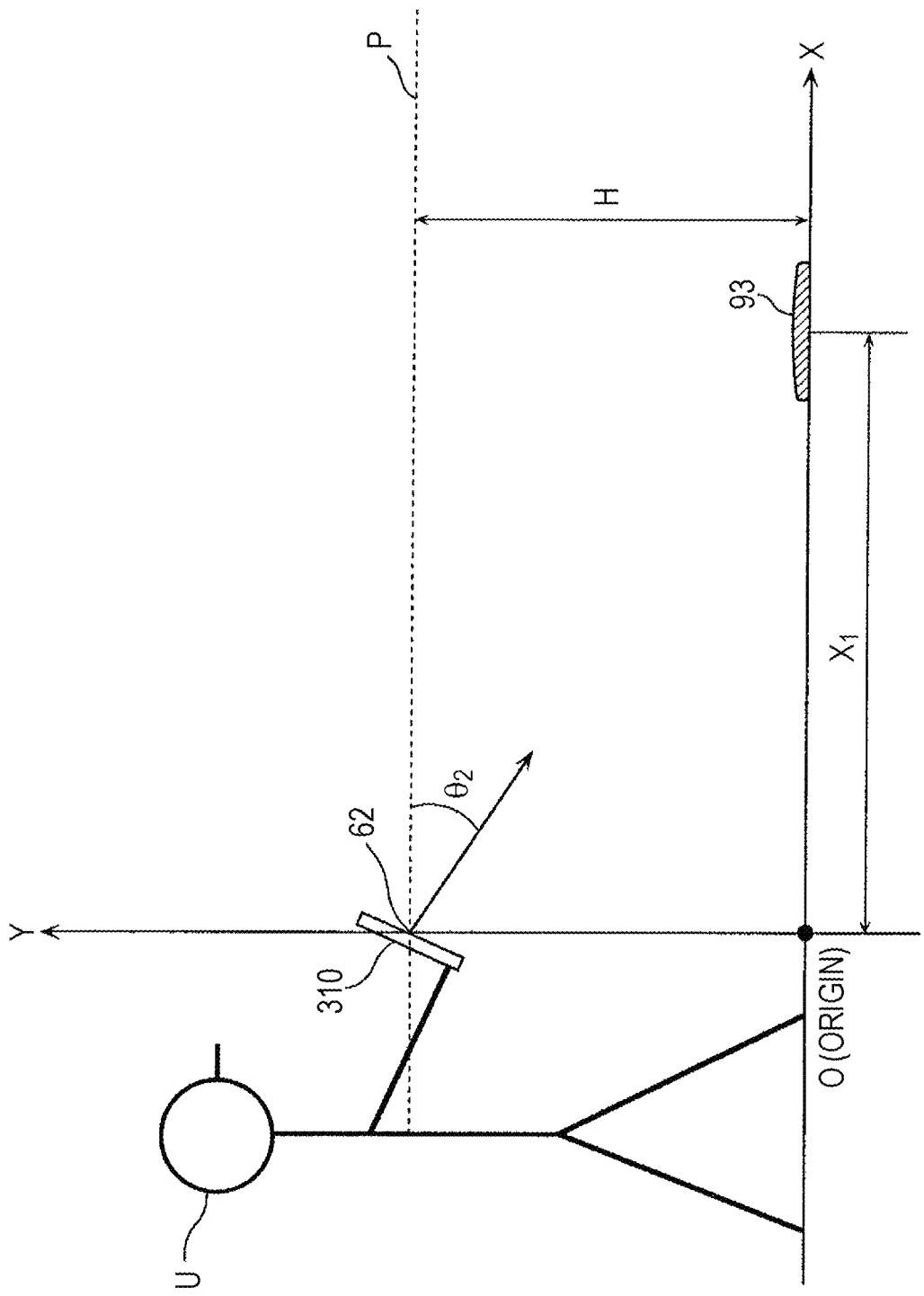
FIG. 19 is a schematic view showing how a cleansing agent is sprayed with the purifying apparatus according to Embodiment 2 having its spray nozzle tilted downward.

FIG. 19 is a schematic view showing how the cleansing agent is sprayed with the purifying apparatus 310 according to Embodiment 2 having its spray nozzle 62 tilted downward. Specifically, FIG. 19 illustrates a case where the cleansing agent is sprayed at an angle of inclination $\theta_2$ pointing toward a lower position than the imaginary plane P.

As mentioned above, the horizontal distance $X_1$ and the height H from the spray nozzle 62 to the physical object 93 are calculated by the controller 340 according to Eq. (1) and Eq. (2), respectively. Further, the angle of inclination $\theta_2$ is an angle determined by the user U in order to spray the cleansing agent, and is detected by the angular sensor 280. The controller 340 uses the horizontal distance $X_1$, the height H, and the angle of inclination $\theta_2$ to calculate the first pressure at which the cleansing agent is sprayed. In Embodiment 2, the controller 340 calculates, as an example of the first pressure, the initial velocity $v_0$ of the cleansing agent that is sprayed from the spray nozzle 62. The following show particular details.

Assuming that $t_A$ is the time required for the cleansing agent to reach the physical object 93 after being sprayed from the spray nozzle 62, the horizontal distance $X_1$ is expressed by Eq. (3):

$$X_1 = t_A \times v_0 \cos\theta_2 \tag{3}$$

Similarly, by integrating the gravitational acceleration g twice, the height H is expressed by Eq. (4):

$$H = \frac{g}{2}t_A^2 + t_A \times v_0 \sin\theta_2 \tag{4}$$

Solving Eq. (4) for $t_A$ causes $t_A$ to be expressed by Eq. (5) as follows:

$$t_A = \frac{-v_0\sin\theta_2 + \sqrt{(v_0\sin\theta_2)^2 + 2gH}}{g} \tag{5}$$

Furthermore, substituting $t_A$, which is expressed by Eq. (5), in Eq. (3) causes the horizontal distance $X_1$ to be expressed by Eq. (6):

$$X_1 = \frac{-v_0\sin\theta_2 + \sqrt{(v_0\sin\theta_2)^2 + 2gH}}{g} \times v_0\cos\theta_2 \tag{6}$$

The horizontal distance $X_1$, which is calculated according to Eq. (6), is equivalent to the distance $X_p$ that the cleansing agent can reach when sprayed at the downward angle of inclination $\theta_2$ and the initial velocity $v_0$. Solving Eq. (6) for the initial velocity $v_0$ causes the initial velocity $v_0$ to be expressed by Eq. (7):

$$v_0 = \sqrt{\frac{gX_1^2}{2\cos\theta_2(H\cos\theta_2 - X_1\sin\theta_2)}} \tag{7}$$

In Eq. (7), the gravitational acceleration g is a constant. The horizontal distance $X_1$ and the height H are values obtained by ranging. The angle of inclination $\theta_2$ is a value that is detected by the angular sensor 280. Accordingly, by using Eq. (7), the controller 340 can calculate the downward initial velocity $v_0$. The controller 340 determines the first pressure $P_A$ so that the cleansing agent is sprayed from the spray nozzle 62 at the initial velocity $v_0$ thus calculated. For example, the controller 340 has stored in a memory a table in which the downward initial velocity $v_0$ and the first pressure $P_A$ are associated with each other in advance and, with reference to the memory, determines the first pressure $P_A$ from the initial velocity $v_0$ thus calculated. Alternatively, the controller 340 may have stored therein a function for determining the first pressure $P_A$ on the basis of the downward initial velocity $v_0$ and calculate the first pressure $P_A$ on the basis of the function.

As can be seen from Eq. (7), $H \cos \theta_2 = X_1 \sin \theta_2 > 0$ needs to be satisfied. That is, on the basis of the relationships of Eq. (1) and Eq. (2), $\theta_2 < \theta_1$ needs to be satisfied.

Figure 20:
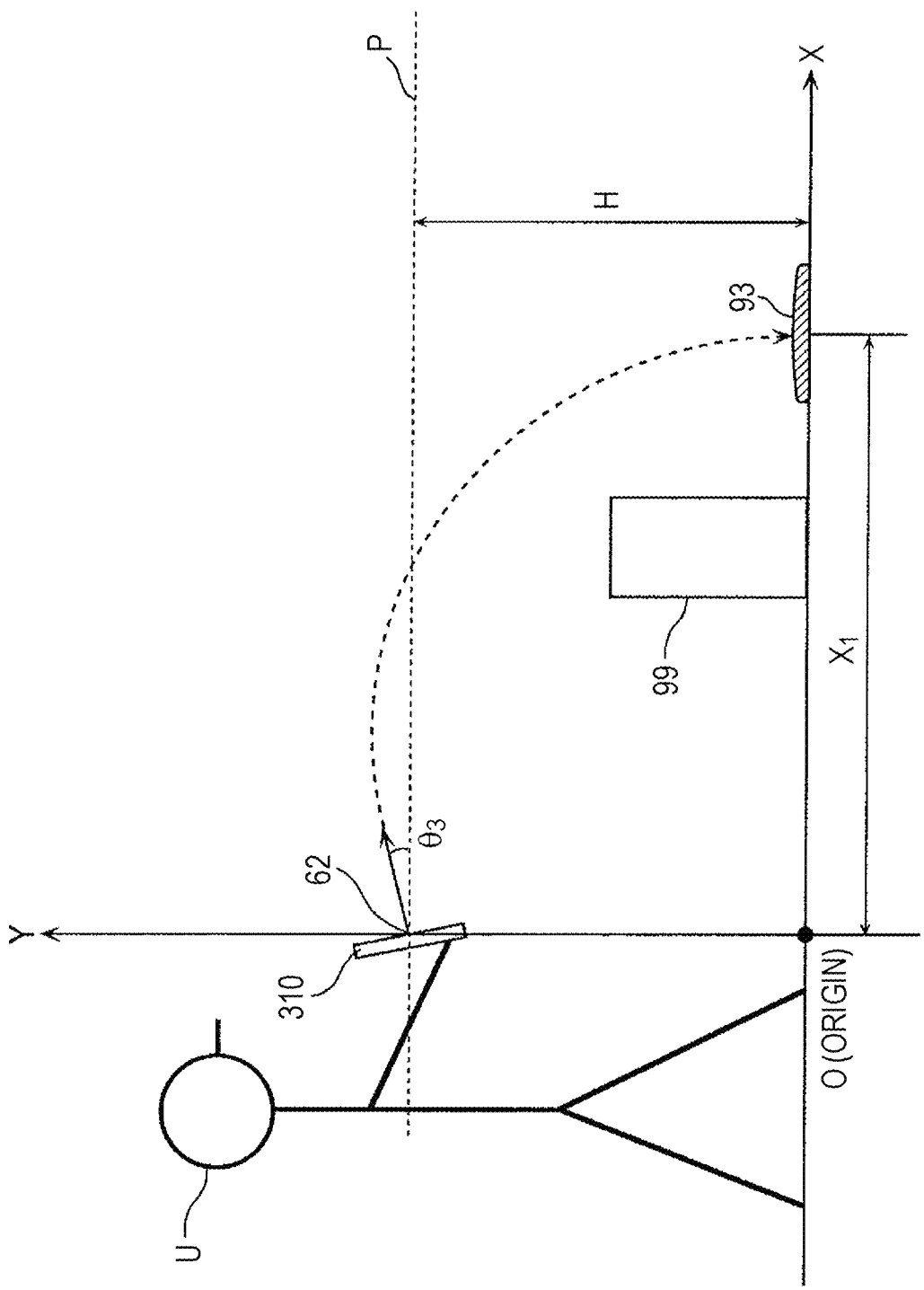
FIG. 20 is a schematic view showing how the cleansing agent is sprayed with the purifying apparatus according to Embodiment 2 having its spray nozzle tilted upward.

Spraying the cleansing agent downward enables the cleansing agent to reach the physical object 93 with a low pressure. Meanwhile, as shown in FIG. 20, in a case where an obstacle 99 is present between the purifying apparatus 310 and the physical object 93, spraying the cleansing agent downward may disable the cleansing agent to reach the physical object 93. In such a case, the user U places the spray nozzle 62 at an upward tilt. This enables the cleansing agent to reach the physical object 93 over the obstacle 99 as indicated by a dotted arrow in FIG. 20.

Examples of the obstacle 99 include, but are not limited to, substances, such as a transparent glass, that do not affect ranging. The obstacle 99 may be a piece of furniture, a household appliance, or an animal such as a pet.

FIG. 20 is a schematic view showing how the cleansing agent is sprayed with the purifying apparatus 310 according to Embodiment 2 tilted upward. Specifically, FIG. 20 illustrates a case where the cleansing agent is sprayed at an angle of inclination $\theta_3$ pointing toward a higher position than the imaginary plane P.

As in the downward case, assuming that $t_B$ is the time required for the cleansing agent to reach the physical object 93 after being sprayed from the spray nozzle 62, the horizontal distance $X_1$ is expressed by Eq. (8):

$$X_1 = t_B \times v_0 \cos \theta_3 \qquad (8)$$

Similarly, by integrating the gravitational acceleration g twice, the height H is expressed by Eq. (9):

$$H = \frac{g}{2} t_B^2 - t_B \times v_0 \sin \theta_3 \qquad (9)$$

As can be seen from a comparison between Eq. (9) and Eq. (4), the sign of a term concerning the initial velocity $v_0$ is negative, as the cleansing agent is sprayed upward. It should be noted the vertically downward direction is positive.

Solving Eq. (9) for $t_B$ causes $t_B$ to be expressed by Eq. (10) as follows:

$$t_B = \frac{v_0 \sin \theta_3 + \sqrt{(v_0 \sin \theta_3)^2 + 2gH}}{g} \qquad (10)$$

Furthermore, substituting $t_B$, which is expressed by Eq. (10), in Eq. (8) causes the horizontal distance $X_1$ to be expressed by Eq. (11):

$$X_1 = \frac{v_0 \sin \theta_3 + \sqrt{(v_0 \sin \theta_3)^2 + 2gH}}{g} \times v_0 \cos \theta_3 \qquad (11)$$

The horizontal distance $X_1$, which is calculated according to Eq. (11), is equivalent to the distance $X_p$ that the cleansing agent can reach when sprayed at the upward angle of inclination $\theta_3$ and the initial velocity $v_0$. Solving Eq. (11) for the initial velocity $v_0$ causes the initial velocity $v_0$ to be expressed by Eq. (12):

$$v_0 = \sqrt{\frac{gX_1^2}{2\cos\theta_3(H\cos\theta_3 + X_1\sin\theta_3)}} \qquad (12)$$

In Eq. (12), the gravitational acceleration g is a constant. The horizontal distance $X_1$ and the height H are values obtained by ranging. The angle of inclination $\theta_3$ is a value that is detected by the angular sensor 280. Accordingly, by using Eq. (12), the controller 340 can calculate the upward initial velocity $v_0$. The controller 340 determines the second pressure $P_B$ so that the cleansing agent is sprayed from the spray nozzle 62 at the initial velocity $v_0$ thus calculated. For example, the controller 340 has stored in a memory a table in which the upward initial velocity $v_0$ and the second pressure $P_B$ are associated with each other in advance and, with reference to the memory, determines the second pressure $P_B$ from the initial velocity $v_0$ thus calculated. Alternatively, the controller 340 may have stored therein a function for determining the second pressure $P_B$ on the basis of the upward initial velocity $v_0$ and calculate the second pressure $P_B$ on the basis of the function.

The tilt of the spray nozzle 62 as determined by the user U may be a horizontal direction. That is, the angle of inclination of the spray nozzle 62 may be 0 degree. In this case, either Eq. (7) or (12) may be used, whereby the same initial velocity $v_0$, i.e. the same pressure, is calculated.

Further, in a case where the physical object 93 is present directly below the spray nozzle 62, the tilt of the spray nozzle 62 may be a perpendicular direction. That is, the angle of inclination of the spray nozzle 62 may be 90 degree. In this case, the pressure may be substantially 0.

The controller 340 may determine the tilt of the spray nozzle 62 according to a combination of a distance measured by the range finder 80 and a pressure at which the spray 260 sprays the cleansing agent. Specifically, the controller 340 may calculate the angle of inclination $\theta_2$ or $\theta_3$ according to Eq. (7) or (12), assuming that the initial velocity $v_0$ is a known value and the angle of inclination $\theta_2$ or $\theta_3$ is an unknown.

Operation

Next, an operation of the purifying apparatus 310 according to Embodiment 2, i.e. a purifying method, is described with reference to FIG. 21.

Figure 21:
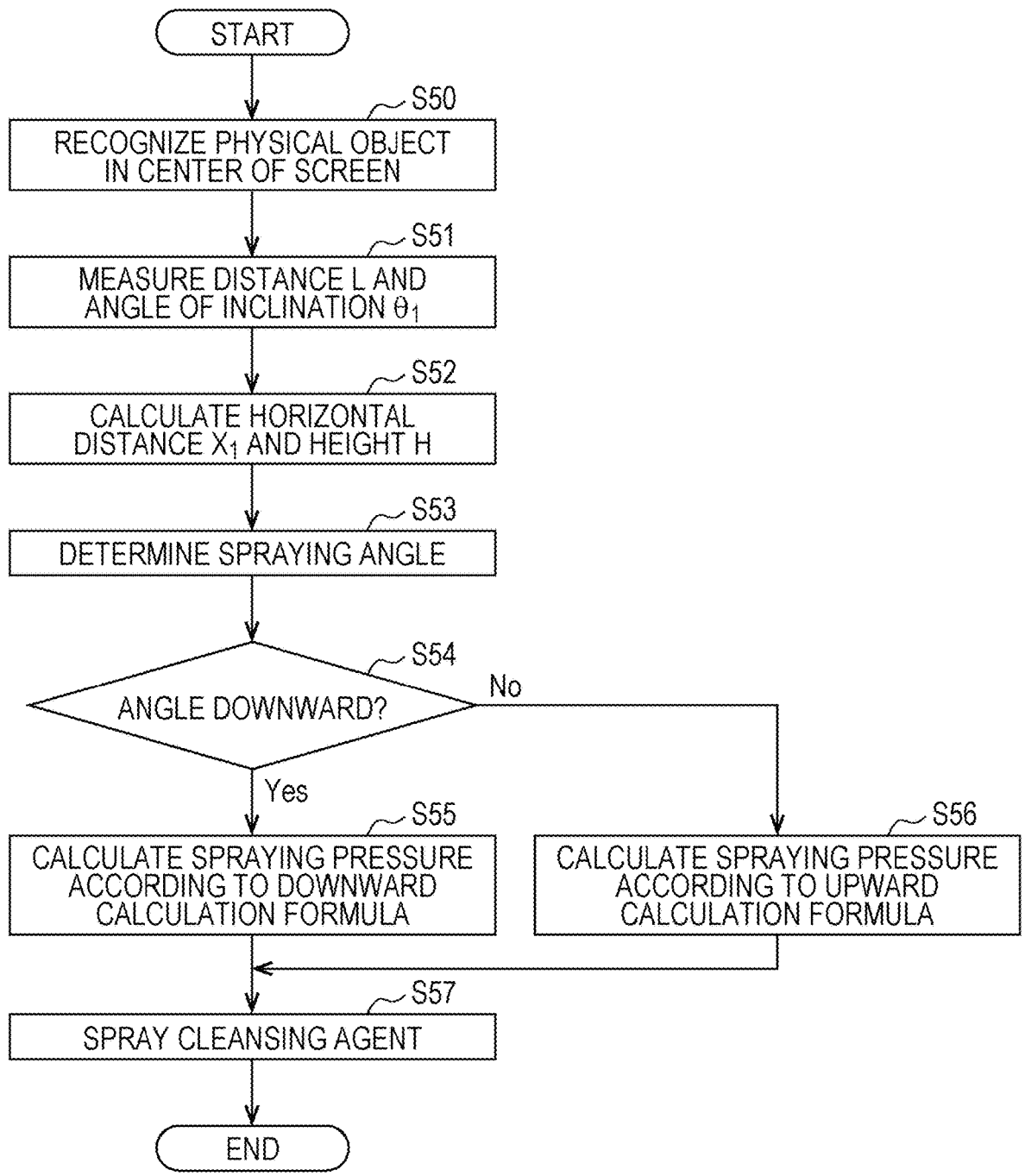
FIG. 21 is a flow chart showing an operation of the purifying apparatus according to Embodiment 2.

FIG. 21 is a flow chart showing an operation of the purifying apparatus 310 according to Embodiment 2. As in the case of Embodiment 1, the purifying apparatus 310 according to Embodiment 2 makes a determination of a physical object 93 first and, after having determined that a physical object 93 is present, then performs the operation shown in FIG. 21. Specifically, the operation shown in FIG. 21 is performed after the process from step S10 to step S12 shown in FIG. 7 has been performed.

First, the controller 340 of the purifying apparatus 310 recognizes the physical object 93 in the center of the screen of the display 50 (S50). Specifically, as shown in FIG. 18B, the controller 340 recognizes the physical object 93 in the center of the screen of the display 50 by accepting an instruction that the user U gives after having placed at least a portion of the physical object 93 in the circular frame 51.

Alternatively, the controller 340 may recognize the placement of the physical object 93 in the circular frame 51 by image processing.

After having recognized the physical object 93, the controller 340 controls the range finder 80 to measure the distance L from the spray nozzle 62 to the physical object 93 and controls the angular sensor 280 to measure the angle of inclination $\theta_1$ of the spray nozzle 62 during ranging (S51). Next, the controller 340 calculates the horizontal distance $X_1$ and the height H according to the aforementioned Eq. (1) and Eq. (2), respectively, on the basis of the distance L and the angle of inclination el and thus measured (S52).

Next, the controller 340 determines an angle at which the cleansing agent is sprayed (S53). For example, the user U determines, in consideration of the presence or absence of an obstacle 99, such a tilt that the cleansing agent reaches the physical object 93, and operates the operation button 70 with the spray nozzle tilted at a tilt thus determined. The controller 340 controls the angular sensor 280 to detect the angle of inclination $\theta_2$ or $\theta_3$ of the spray nozzle 62 at the point of time at which the operation button 70 was operated.

In a case where the angle of inclination thus detected is a downward angle (Yes in S54), the controller 340 calculates, according to a downward calculation formula, the first pressure $P_A$ at which the cleansing agent is sprayed (S55). Specifically, the controller 340 calculates the initial velocity $v_0$ according to the aforementioned Eq. (7) on the basis of the angle of inclination $\theta_2$ thus detected and the horizontal distance $X_1$ and the height H thus calculated and determines the first pressure $P_A$ on the basis of the initial velocity $v_0$ thus calculated.

In a case where the angle of inclination thus detected is an upward angle (No in S54), the controller 340 calculates, according to an upward calculation formula, the second pressure $P_B$ at which the cleansing agent is sprayed (S56). Specifically, the controller 340 calculates the initial velocity $v_0$ according to the aforementioned Eq. (12) on the basis of the angle of inclination $\theta_3$ thus detected and the horizontal distance $X_1$ and the height H thus calculated and determines the second pressure $P_B$ on the basis of the initial velocity $v_0$ thus calculated.

Next, the controller 340 controls the spray 260 so that the spray 260 sprays the cleansing agent at the first pressure $P_A$ or second pressure $P_B$ thus determined (S57). Before the cleansing agent is actually sprayed, the display 50 may display a trajectory of reach of the cleansing agent from the spray nozzle 62 to the physical object 93 and/or the pressure. A specific example of the trajectory of reach will be described in the after-mentioned Modification 2 of Embodiment 2.

MODIFICATIONS

The following describes modifications of Embodiment 2 described above. It should be noted that the following modifications give a description with a focus on differences from Embodiment 2 and omit or simplify a description of common features.

Modification 1

Embodiment 2 has shown an example in which the initial velocity $v_0$, which is equivalent to the pressure at which the cleansing agent is sprayed from the spray nozzle 62, is calculated; meanwhile, in Modification 1 of Embodiment 2, the initial velocity $v_0$ is for example a predetermined value and a value whose change is restricted. For example, the initial velocity $v_0$ may be a totally-unchangeable fixed value or may be a value selected from among a plurality of graded candidate values.

Due to the restriction on the initial velocity $v_0$, a determination of the tilt of the spray nozzle 62 by the user U may disable the cleansing agent to reach the physical object 93 with that tilt. Even in such a case, the purifying apparatus according to Modification 1 of Embodiment 2 enables the cleansing agent to reach the physical object 93. It should be noted a configuration of the purifying apparatus according to Modification 1 of Embodiment 2 is the same as that of the purifying apparatus 310 according to Embodiment 2 and therefore is not described below.

Figure 22:
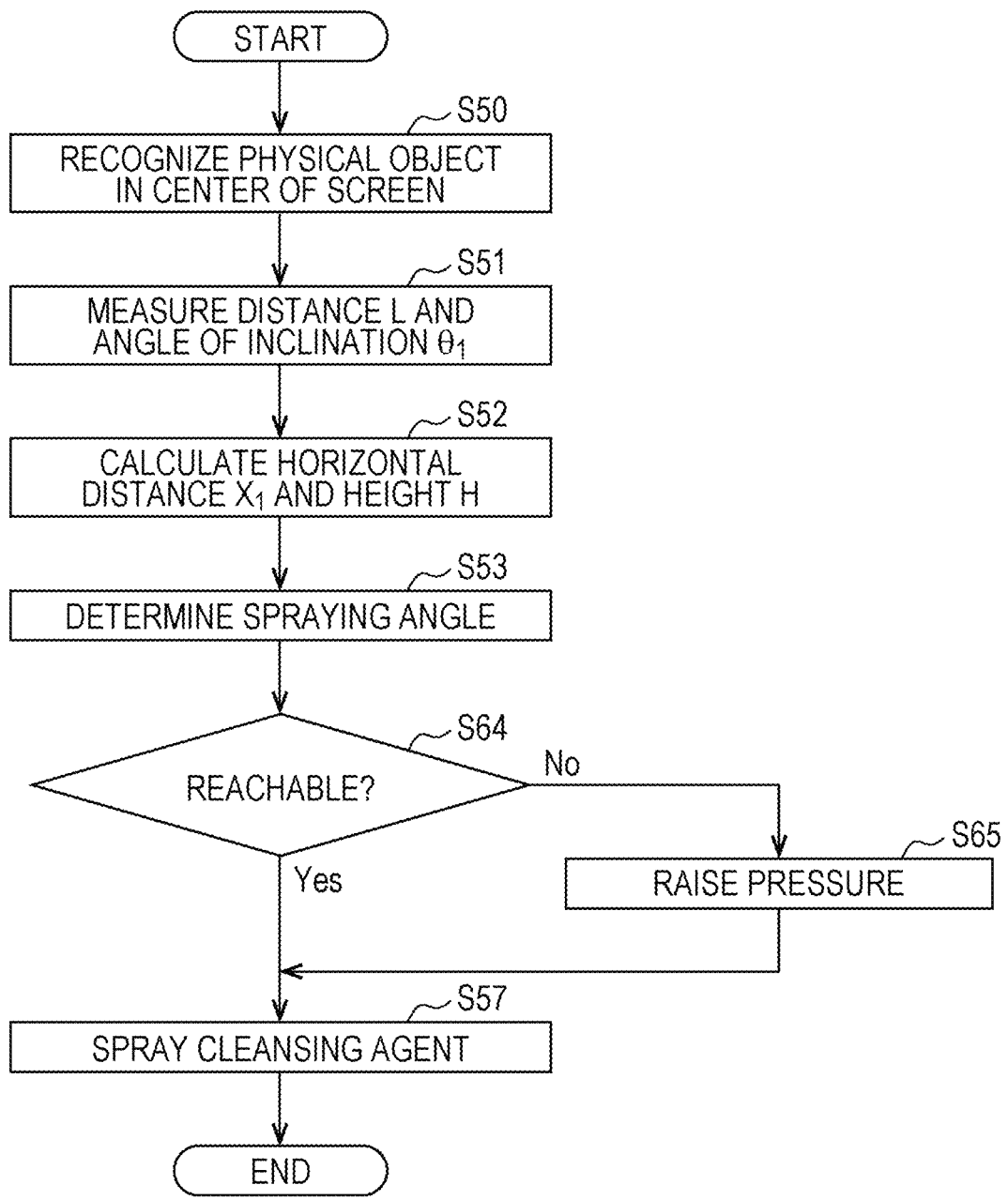
FIG. 22 is a flow chart showing an operation of a purifying apparatus according to Modification 1 of Embodiment 2.

FIG. 22 is a flow chart showing an operation of the purifying apparatus 310 according to Modification 1 of Embodiment 2. As shown FIG. 22, the process up to the step (S53) of determining an angle at which the cleansing agent is sprayed is the same as that of Embodiment 2.

As shown in FIG. 22, the controller 340 determines whether the cleansing agent can reach the physical object 93 when sprayed at the angle thus determined (S64). Specifically, the controller 340 calculates, according to Eq. (6) or (11), the distance $X_p$ that the cleansing agent can reach when sprayed at the angle thus determined.

In a case where the distance $X_p$ thus calculated is shorter than $X_1$ represented by Eq. (1), the controller 340 determines that the cleansing agent cannot reach the physical object 93 (No in S64). In this case, in a case where the pressure has not reached its upper limit and can be raised, the controller 340 raises the pressure to a value that allows the cleansing agent to reach the physical object 93 (S65). Since the rise in pressure has allowed the cleansing agent to reach the physical object 93, the controller 340 controls the spray 260 so that the spray 260 sprays the cleansing agent toward the physical object 93 through the spray nozzle 62 (S57).

In a case where the distance $X_p$ thus calculated is greater than $X_1$ represented by Eq. (1), the controller 340 determines that the cleansing agent can reach the physical object 93 (Yes in S64). Since the cleansing agent can reach the physical object 93, the controller 340 controls the spray 260 so that the spray 260 sprays the cleansing agent toward the physical object 93 through the spray nozzle 62 (S57).

In a case where the pressure is totally unchangeable or in a case where the upper limit of a changeable pressure has been reached, the cleansing agent cannot reach the physical object 93 with that pressure when it has been determined that the cleansing agent cannot reach the physical object 93 (No in S64). To address this problem, the purifying apparatus 310 according to Modification 1 of Embodiment 2 may give an instruction to the user U as shown in FIG. 23.

Figure 23:
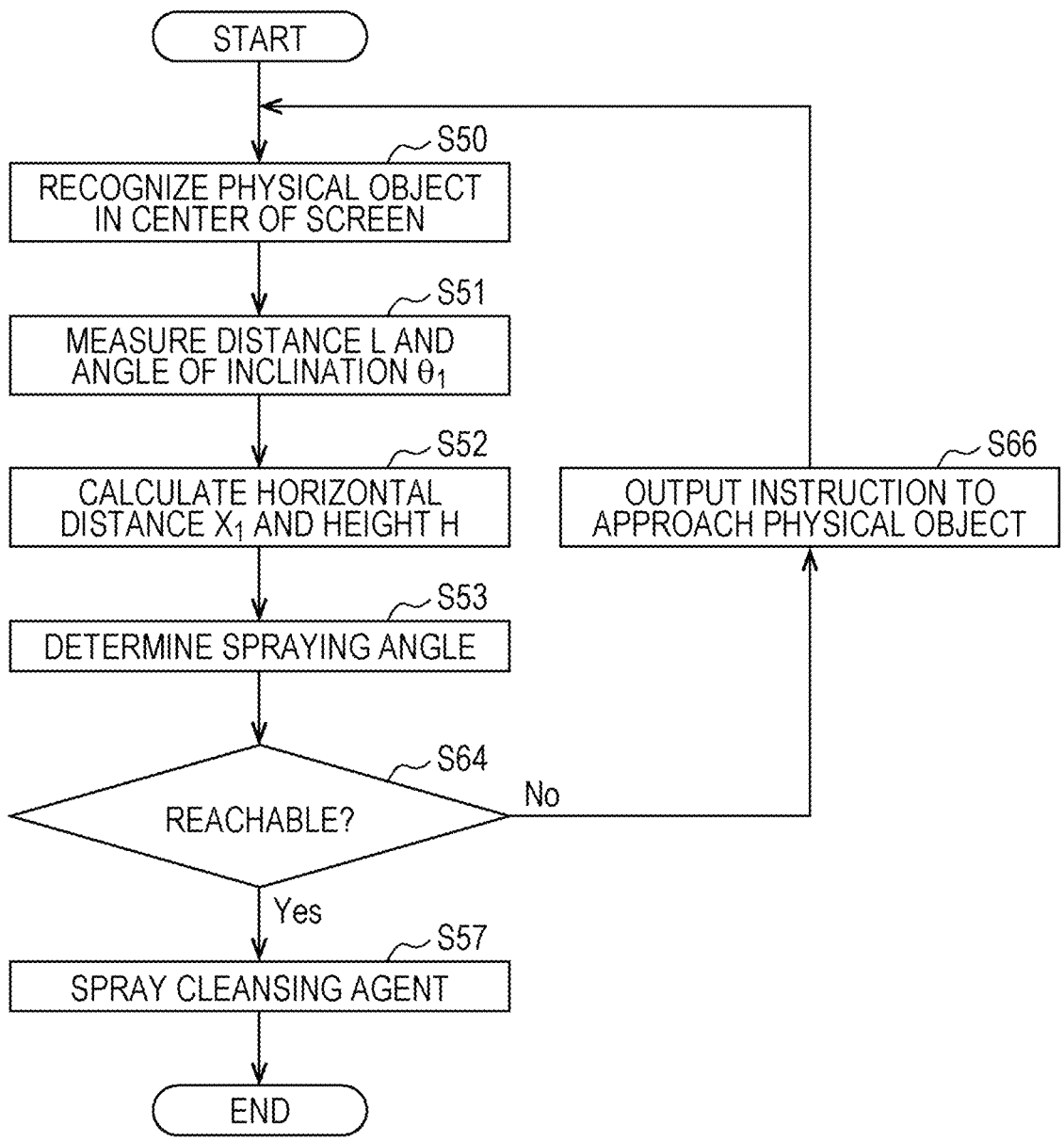
FIG. 23 is a flow chart showing another example of an operation of the purifying apparatus according to Modification 1 of Embodiment 2.

FIG. 23 is a flow chart showing another example of an operation of the purifying apparatus 310 according to Modification 1 of Embodiment 2. As shown in FIG. 23, in a case where it has been determined that the cleansing agent cannot reach the physical object 93 (No in S64), the controller 340 outputs an instruction that prompts the user U to approach the physical object 93 (S66). Specifically, the controller 340 displays a text message that prompts the user U to approach the physical object 93. At this point in time, the display 50 may display the distance $X_p$ that allows the cleansing agent to reach the physical object 93. Since a movement of the user U effects a change in positional relationship between the spray nozzle 62 and the physical object 93, the purifying apparatus 310 repeatedly performs the process from the step (S50) of recognizing the physical object 93 for ranging.

Alternatively, the controller 340 may give a voice instruction that prompts the user U to approach. For example, the purifying apparatus 310 may has a voice outputter such as a speaker, and the controller 340 may output, through the speaker, a voice that prompts the user U to approach.

Modification 2

Next, Modification 2 of Embodiment 2 is described.

A purifying apparatus according to Modification 2 of Embodiment 2 displays, on the display 50, a trajectory of reach of the cleansing agent from the spray nozzle 62 to the physical object 93 and thereby gives the user U a pre-spraying schematic presentation of how the cleansing agent is sprayed. Further, by displaying a plurality of trajectories of reach, the user U is allowed to select a trajectory of reach along which actual spraying occurs. It should be noted that a configuration of the purifying apparatus according to Modification 2 of Embodiment 2 is the same as that of the purifying apparatus 310 according to Embodiment 2 and therefore is not described below.

Figure 24:
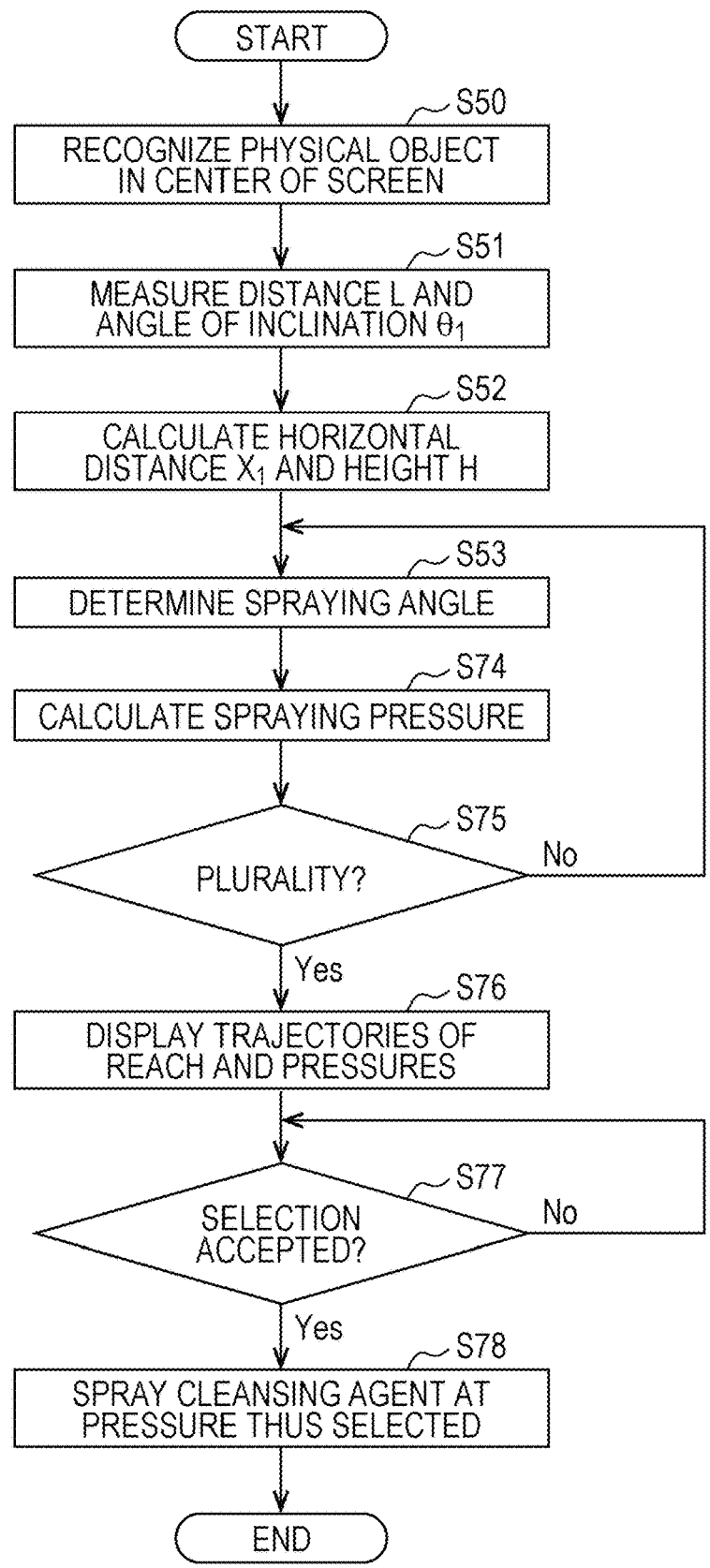
FIG. 24 is a flow chart showing an operation of a purifying apparatus according to Modification 2 of Embodiment 2.

FIG. 24 is a flow chart showing an operation of the purifying apparatus 310 according to Modification 2 of Embodiment 2. As shown FIG. 24, the process up to the step (S53) of determining an angle at which the cleansing agent is sprayed is the same as that of Embodiment 2.

The controller 340 calculates, on the basis of the angle thus determined, a pressure at which the cleansing agent is sprayed (S74). The specific calculating method is the same as that of Embodiment 2. In a manner similar to step S55 or S56 of FIG. 21, the controller 340 calculates the pressure at which the cleansing agent is sprayed.

In Modification 2 of Embodiment 2, the controller 340 calculates pressures that correspond to a plurality of angles of inclination. For this reason, in a case where one or less pressure has been calculated (No in S75), the controller 340 returns to step S53 to let the user U choose a different angle of inclination. Although, in Modification 2 of Embodiment 2, the plurality of angles of inclination may include at least one angle pointing toward a lower position than the imaginary plane P and at least one angle pointing toward a higher position than the imaginary plane P, this is not intended to impose any limitation. The plurality of angles of inclination may include only a downward angle or may include only an upward angle.

After a plurality of pressures have been calculated (Yes in S75), the controller 340 generates trajectories of reach for each separate pressure and displays them on the display 50 (S76). For example, the controller 340 displays a trajectory display screen 350 shown in FIG. 25.

Figure 25:
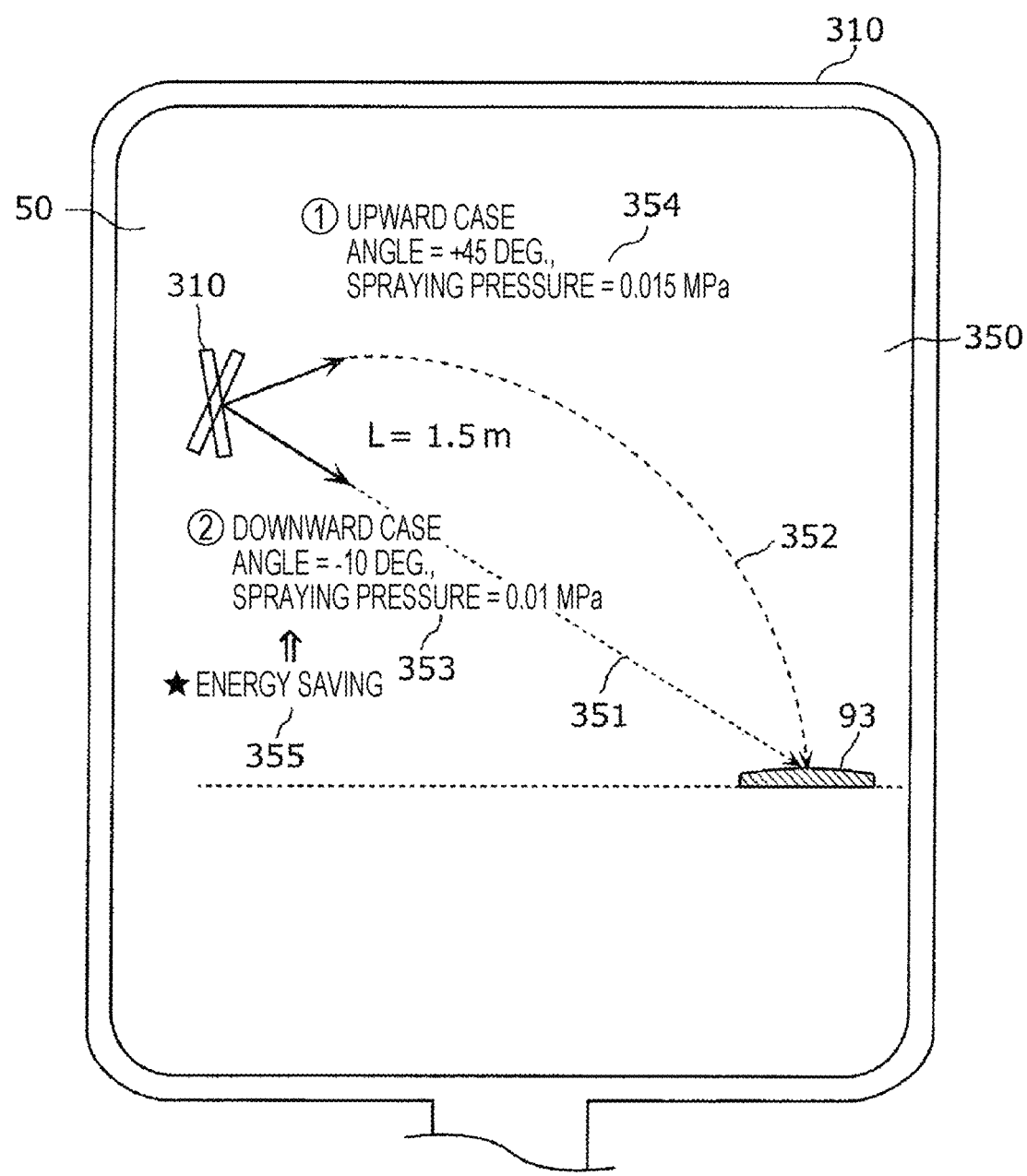
FIG. 25 is a diagram showing an example of a trajectory display screen that is displayed on a display of the purifying apparatus according to Modification 2 of Embodiment 2.

FIG. 25 is a diagram showing an example of the trajectory display screen 350 that is displayed on the display 50 of the purifying apparatus 310 according to Modification 2 of Embodiment 2. The trajectory display screen 350 contains the purifying apparatus 310 with the spray nozzle 62 and the physical object 93. Display positions of the spray nozzle 62 and the physical object 93 are determined on the basis of the horizontal distance $X_1$ and the height H thus calculated.

When the downward first pressure $P_A$ has been calculated, the display 50 displays a first trajectory of reach 351 from the spray nozzle 62 to the physical object 93. At this point in time, as shown in FIG. 25, the display 50 may display first pressure information 353. The first pressure information 353 is text information that indicates the first pressure $P_A$ thus calculated.

Further, when the upward second pressure $P_B$ has been calculated, the display 50 displays a second trajectory of reach 352 from the spray nozzle 62 to the physical object 93. At this point in time, as shown in FIG. 25, the display 50 may display second pressure information 354. The second pressure information 354 is text information that indicates the second pressure $P_B$ thus calculated.

In the example shown in FIG. 25, the display 50 further shows recommendation information 355. The recommendation information 355 is information that recommends selection of the first trajectory of reach 351. Specifically, the recommendation information 355 is, but is not limited to, text information "ENERGY SAVING". The recommendation information 355 may also be text information "RECOMMENDED". Alternatively, without being limited to text information, the recommendation information 355 may be expressed by a mode of display of the first trajectory of reach 351 or the first pressure information 353. The mode of display may include an emphasizing process that effects a highlighting display or a blinking display.

The recommendation information 355 may be information that recommends selection of the second trajectory of reach 352. The downward initial velocity $v_0$ represented by Eq. (7) and the upward initial velocity $v_0$ represented by Eq. (12) are different in magnitude relationship according to the tilt of the spray nozzle 62. That is, the downward first pressure $P_A$ and the upward second pressure $P_B$ are different in magnitude relationship according to the magnitudes of the angles of inclination $\theta_2$ and $\theta_3$ of the spray nozzle 62. The recommendation information 355 may recommend selection of a trajectory of reach with a lower pressure from among the first pressure $P_A$ and the second pressure $P_B$.

In Modification 2 of Embodiment 2, the trajectory display screen 350 shown in FIG. 25 functions also as a screen for selecting a trajectory of reach. Specifically, the user U selects one trajectory of reach from among the plurality of trajectories of reach by operating the operation button 70 or the touch panel display 50.

As shown in FIG. 24, when the first trajectory of reach 351 and the second trajectory of reach 352 have been simultaneously displayed on the display 50, the controller 340 accepts selection of either the first trajectory of reach 351 or the second trajectory of reach 352 (Yes in S77). The controller 340 causes the cleansing agent to be sprayed from the spray nozzle 62 at a pressure that corresponds to the trajectory of reach thus selected (S78). For example, in a case where the first trajectory of reach 351 has been selected, the controller 340 causes the cleansing agent to be sprayed at the first pressure $P_A$. In a case where the second trajectory of reach 352 has been selected, the controller 340 causes the cleansing agent to be sprayed at the second pressure $P_B$.

The controller 340 remains in a waiting state until it accepts a selection (No in S77). Alternatively, in a case where no selection is made even when a predetermined period of time elapses, the controller 340 returns to step S53 to start over again from a determination of the tilt of the spray nozzle 62. Alternatively, the controller 340 may accept an instruction to redo a display of a trajectory of reach and, upon accepting the instruction, may return to step S53 to start over again from a determination of the tilt of the spray nozzle 62.

Although Modification 2 of Embodiment 2 has shown an example in which the trajectory display screen 350 is utilized as a selection screen, this is not intended to impose any limitation. The trajectory display screen 350 may be displayed for the user U to check. In this case, only either the first trajectory of reach 351 or the second trajectory of reach 352 may be displayed. At least one of the first pressure information 353, the second pressure information 354, and the recommendation information 355 does not need to be displayed.

Other Embodiments

In the foregoing, purifying apparatuses according to one or more aspects have been described with reference to embodiments; however, the present disclosure is not intended to be limited to these embodiments. Applications to the present embodiments of various types of modification conceived of by persons skilled in the art and embodiments constructed by combining constituent elements of different embodiments are encompassed in the scope of the present disclosure, provided such applications and embodiments do not depart from the spirit of the present disclosure.

For example, the purifying apparatus according to any of the embodiments or modifications described above may be non-portable. For example, the purifying apparatus may be a stationary purifying apparatus installed indoors or the like. At least one of the optical sensor, the determination circuit, the spray, and the range finder may be provided as a separate entity.

For example, although each of the embodiments described above has shown an example in which the purifying apparatus detects fluorescence that is emitted from a physical object, this is not intended to impose any limitation. For example, the purifying apparatus may detect light reflected or scattered by a physical object. For example, the purifying apparatus may detect light reflected or scattered by particles that constitute a physical object or moisture contained in a physical object. The purifying apparatus can detect a physical object with high accuracy by measuring in advance light reflected or scattered by a background component in a case where no physical object is present. Further, the purifying apparatus may detect a Raman spectrum obtained by moisture contained in a physical object.

Further, for example, the photodetector may include a photoreceptor of one pixel instead of the image sensor. By a user passing the purifying apparatus over a target region while tilting the purifying apparatus in various directions, the presence or absence of a physical object in the target region can be determined.

Further, for example, in an embodiment, no change in excitation wavelength or observation wavelength needs to be effected in a case where it is only necessary to be able to detect only an amino acid. That is, the purifying apparatus 10 according to an embodiment does not need to generate fluorescence fingerprints but need only set, according to a combination of an excitation wavelength and a fluorescence wavelength that corresponds to an amino acid, the wavelength of light that the light source 31 emits and an observed wavelength at which the photodetector 32 receives light. Specifically, the light source 31 needs only emit excitation light with a peak at around 280 nm as the first light. The photodetector 32 needs only receive light through a filter having a transmission band, for example, at around 320 nm.

Further, for example, although an amino acid contained in a physical object has been shown as an example of an organic substance, this is not intended to impose any limitation. For example, the purifying apparatus may determine the presence or absence of a physical object by detecting fluorescence that is emitted by vitamins or NADH (nicotinamide adenine dinucleotide).

For example, vitamin A produces fluorescence with a peak at 425 nm upon irradiation with excitation light 13 at a wavelength of 325 nm. Vitamin B2 produces fluorescence with a peak at 520 nm upon irradiation with excitation light at a wavelength of 450 nm. NADH produces fluorescence with a peak at 460 nm upon irradiation with excitation light at an excitation wavelength of 350 nm.

Further, for example, the present disclosure can also be achieved as a purifying method including, as steps, the processes that the determination circuit, the spray, or other components of a purifying apparatus according to each embodiment perform.

It should be noted that the present disclosure cannot only be realized as a purifying method but can also be realized as a program for causing a computer to execute steps of the light observation method and a recording medium, such as a DVD (digital versatile disc), storing the program. The aforementioned steps are achieved by the computer reading and executing the program stored on the recording medium. The program may be stored in advance on the recording medium or may be supplied to a recording medium via a wide area communication network including the Internet.

Further, in each of the embodiments described above, each of the constituent elements of the purifying apparatus may be configured by dedicated hardware or may be realized by executing a software program suited to that constituent element. Each of the constituent elements may be realized by a program executor such as a CPU (central processing unit) or a processor reading and executing a software program stored on a recording medium such as a hard disk or a semiconductor memory.

At this point in time, the processor is not limited in type, provided that it can fulfill a function by executing the program. For example, the processor is constituted by one or more electronic circuits including a semiconductor integrated circuit such as an IC (integrated circuit) or an LSI (large-scale integrated circuit). The plurality of electronic circuits may be integrated into a single chip or may be provided on a plurality of chips. The plurality of chips may be consolidated into a single device or may be decentrally provided in a plurality of devices.

It should be noted that general or specific embodiments may be implemented as a system, an apparatus, an integrated circuit, a computer program, a computer-readable recording medium, or any selective combination thereof.

Further, each of the embodiments described above is subject to various changes, substitutions, additions, omissions, and the like in the scope of the claims or the scope of equivalents thereof.

What is claimed is:

1. A purifying apparatus comprising:
    an optical sensor that outputs an electrical signal, the optical sensor including a light source that emits first light and a photodetector that receives second light from a region irradiated with the first light;
    a determination circuit that determines presence or absence of a physical object in the region and generates an image representing a determination result, the determination circuit including a signal processing circuit that processes the electrical signal;
    a spray that sprays a cleansing agent through a spray nozzle, the spray including the spray nozzle;
    a range finder that measures a distance from the spray nozzle to the physical object; and
    a controller that controls, according to the distance, spraying of the cleansing agent by the spray.

2. The purifying apparatus according to claim 1, further comprising an angular sensor that detects a tilt of the spray nozzle with respect to an imaginary plane that is perpendicular to a direction of gravitational force,
    wherein the controller controls, according to either a combination of the distance and a pressure at which the spray sprays the cleansing agent or a combination of the distance and the tilt of the spray nozzle, conditions under which the cleansing agent is sprayed.

3. The purifying apparatus according to claim 2, wherein the controller accepts a first choice of a tilt during spraying by a user, the first choice of the tilt during spraying being a tilt of the spray nozzle with respect to the imaginary plane during spraying of the cleansing agent, in a case where the tilt during spraying is a tilt pointing to a lower position than the imaginary plane, the controller calculates a first pressure that allows the cleansing agent to reach the physical object, and causes the cleansing agent to be sprayed from the spray nozzle at the first pressure, and in a case where the tilt during spraying is a tilt pointing toward a higher position than the imaginary plane, the controller calculates a second pressure that is higher than the first pressure, and causes the cleansing agent to be sprayed from the spray nozzle at the second pressure.

4. The purifying apparatus according to claim 3, further comprising a display that displays a first trajectory of reach from the spray nozzle to the physical object when the first pressure has been calculated and that displays a second trajectory of reach from the spray nozzle to the physical object when the second pressure has been calculated.

5. The purifying apparatus according to claim 4, wherein the display displays the first trajectory of reach and the first pressure when the first pressure has been calculated and displays the second trajectory of reach and the second pressure when the second pressure has been calculated.

6. The purifying apparatus according to claim 4, wherein the controller further accepts a second choice of the tilt during spraying by the user, in a case where the tilt during spraying of the first choice is a tilt pointing toward a lower position than the imaginary plane and the tilt during spraying of the second choice is a tilt pointing toward a higher position than the imaginary plane or in a case where the tilt during spraying of the first choice is a tilt pointing toward a higher position than the imaginary plane and the tilt during spraying of the second choice is a tilt pointing toward a lower position than the imaginary plane, the display simultaneously displays the first trajectory of reach and the second trajectory of reach, and the controller accepts selection of either the first trajectory of reach or the second trajectory of reach and causes the cleansing agent to be sprayed from the spray nozzle at a pressure that corresponds to the trajectory of reach thus selected.

7. The purifying apparatus according to claim 6, wherein the display displays recommendation information that recommends selection of the first trajectory of reach.

8. The purifying apparatus according to claim 1, wherein the first light is excitation light that excites the physical object, and the second light is fluorescence that the physical object emits upon irradiation with the excitation light.

9. The purifying apparatus according to claim 8, wherein the determination circuit determines the presence or absence of the physical object based on a combination of a wavelength of the fluorescence and a wavelength of the excitation light.

10. The purifying apparatus according to claim 1, wherein the determination circuit determines the presence or absence of the physical object based on a result of a comparison between an intensity of the second light received by the photodetector and a threshold.

11. The purifying apparatus according to claim 1, wherein the determination circuit determines the presence or absence of the physical object based on a component of the second light whose wavelength is longer than a wavelength of the first light.

12. The purifying apparatus according to claim 1, wherein the physical object is vomit, excrement, or body fluids.

13. The purifying apparatus according to claim 1, wherein the cleansing agent is a sodium hypochlorite formulation or an alcohol formulation.

* * * * *